(12) United States Patent
Rodman

(10) Patent No.: US 6,391,635 B1
(45) Date of Patent: May 21, 2002

(54) MONOCLONAL HUMAN NATURAL ANTIBODIES

(75) Inventor: Toby C. Rodman, New York, NY (US)

(73) Assignee: Institute for Human Genetics and Biochemistry, Geneva (CH)

( * ) Notice: Subject to any disclaimer, the term of this patent is extended or adjusted under 35 U.S.C. 154(b) by 0 days.

(21) Appl. No.: 09/577,185

(22) Filed: May 23, 2000

Related U.S. Application Data

(63) Continuation-in-part of application No. 09/198,889, filed on Nov. 24, 1998, now abandoned.
(60) Provisional application No. 60/066,464, filed on Nov. 24, 1997.

(51) Int. Cl.$^7$ .................................................. C12N 1/34
(52) U.S. Cl. ........................ 435/346; 435/325; 435/326; 435/328; 435/329; 435/337; 435/339.1; 530/387.5; 530/388.1; 530/388.15; 530/388.25; 530/388.35
(58) Field of Search ................................. 435/325, 326, 435/328, 329, 337, 339.1, 346; 530/387.5, 388.1, 388.15, 388.25, 388.35

(56) References Cited

U.S. PATENT DOCUMENTS

| | | | |
|---|---|---|---|
| 4,997,764 A | 3/1991 | Dalla Favera | |
| 5,606,026 A | 2/1997 | Rodman | |
| 5,656,272 A | 8/1997 | Le et al. | |

OTHER PUBLICATIONS

Rodman et al. "Epitopes for Natural Antibodies of Human Immunodeficiency Virus (HIV)–Negative (Normal) and HIV–Positive Sera are Coincident with Two Key Functional Sequences of HIV Tat Protein" Proceedings of the National Academy of Sciences of the United States of America, vol. 90, No. 16 (1993), pp. 7719–7723. Q11.N26.*

Jahn et al. "Human hybridomas derived from CD5+ B lymphocytes of patients with chronic lymphocytic leukemia (B–CLL) produce multi–specific nature IGM (kappa) antibodies" Clin. Exp. Immunol., vol. 83(1991), pp. 413–417. RC583.C54.*

Manchester et al., Lactoferrin–Reactive Natural Antibodies, Annals New York Acad. of Sciences, 815:475 (1997).

Lachgar et al., Repair of the in Vitro HIV–1–Induced Immunosuppression and Blockade of the Generation of Functional Suppressive CD8 Cells by Anti–Alpha Interferon and ANTIT–TAT Antibodies, Biomed & Pharmacother. 50:13–18 (1996).

Brocke et al., Treatment of Experimental Encephalomyelitis with a Peptide Analogue of Myelin Basic Protein, Nature 379:343–46 (1996).

Re et al., Effect of Antibody to HIV–1 TAT Protein on Viral Replication in Vitro and Progression of HIV–1 Disease in Vivo, J. Acq. Imm. Def. Syndromes and Human Retrovir. 10:408–416 (1995).

Friedman et al., Predicting Molecular Interactions and Inducible Complementarity: Fragment Docking of Fab–Peptide Complexes, Proteins: Structure, Function and Genetics 20:15–24 (1994).

Coffman et al., Mechanism and Regulation of Immunoglobulin Isotype Switching, Advances in Immuno. 54:229–70 (1993).

Rodman et al., Human Immunodeficiency Virus (HIV) TAT–Reactive Antibodies Present in Normal HIV–Negative Sera and Depleted in HIV–Positive Sera. Identification of the Epitope, J. Exp. Med. 175:1247–53 (1992).

Varela et al., Population Dynamics of Natural Antibodies in Normal and Autoimmune Individuals, Proc. Natl. Acad. Sci. USA 88:5917–21 (1991).

Avrameas, Natural Autoantibodies: from 'Horror Autotoxicus' to 'GNOTHI SEAUTON', Goday 12:154–160 (1991).

Urlacher et al., IgM Anti–Idiotypes that Block Anti–HLA Antibodies: Naturally Occurring or Immune Antibodies?, Clin. Exp. Immunol. 83:116–120 (1991).

Rodman et al., Identification of a Low–Affinity Subset of Protamine–Reactive IgM Antibodies Prsent in Normal, Deficient in AIDS, SERA: Implications of HIV Latency, Cl. Immun. and Immunopath. 57:430–440 (1990).

Posner et al., The Construction and Use of a Human–Mouse Myeloma Analogue Suitable for the Routine Production of Hybridomas Secreting Human Monoclonal Antibodies, Hybridoma 6:611–625 (1987).

Muñoz et al., New Experimental Criteria for Optimization of Solid–Phase Antigen Concentration and Stability in ELISA, J. Immuno. Methods 94:137–144 (1986).

Rodman et al., Naturally Occurring Antibodies Reactive with Sperm Proteins: Apparent Deficiency in AIDS SERA, Science 228:1211–15 (1985).

Rodman et al., p15, A Nuclear–Associated Protein of Human Sperm: Identification of Four Variants and Their Occurrence in Normal and Abnormal Seminal Cells, Gamete Research 8:129–47 (1983).

Goodman et al., Immunological Identification of Lactoferrin as a Shared Antigen on Radioiodinated Human Sperm Surface and in Radioiodinated Human Seminal Plasma, J. Repro. Immuno, 3:99–108 (1981).

Hekman et al., The Antigens of Human Seminal Plasma (with Special Reference to Lactoferrin as a Spermatozoa––Coating Antigen), Protides Biol. Fluids 16:549 (1969).

* cited by examiner

Primary Examiner—Jeffrey Stucker
(74) Attorney, Agent, or Firm—Darby & Darby

(57) ABSTRACT

Disclosed herein are method for producing hydridoma cell lines producing monoclonal human natural IgM antibodies and hybridoma cells produced by the methods. The antibodies are the monoclonal equivalents of circulating human natural antibodies.

6 Claims, 16 Drawing Sheets

FIG. 5

1. MEPVDPRLEPWK
2. LEPWKHPGSQPK
3. GSQPKTACTNCY
4. CTNCYCKKCCFH
5. KCCFHCQVCFIT
6. VCFITCALGISY
7. LGISYGRKKRRQ
8. GRKKRRQRRRPP
9. KKRRQRPRRPQG
10. RPPQGSQTHQVS
11. THQVSLSKQPTS
12. KQPTSQRGDPTE

FIG. 12A
1. MEPVDPRLEPWK
2. LEPWKHPGSQPK
3. GSQPKTACTNCY
4. CTNCYCKKCCFH
5. KCCFHCQVCFIT
6. VCFITKALGISY
7. LGISYGRKKRRQ
8. GRKKRRQRRRPP
9. KKRRQRRRPPQG
10. RPPQGSQTHQVS
11. THQVSLSKQPTS
12. KQPTSQSRGDPT
FIG. 12B
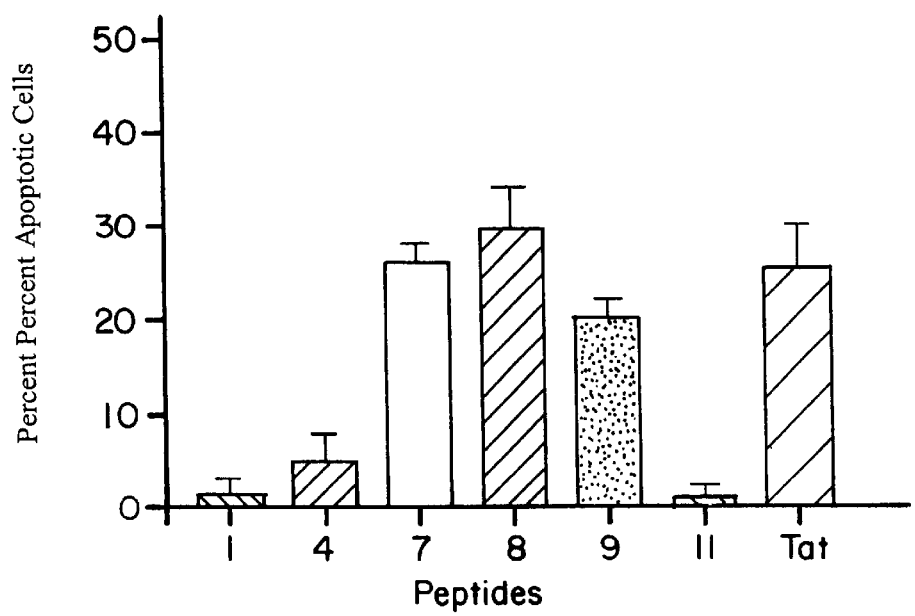
FIG. 12C
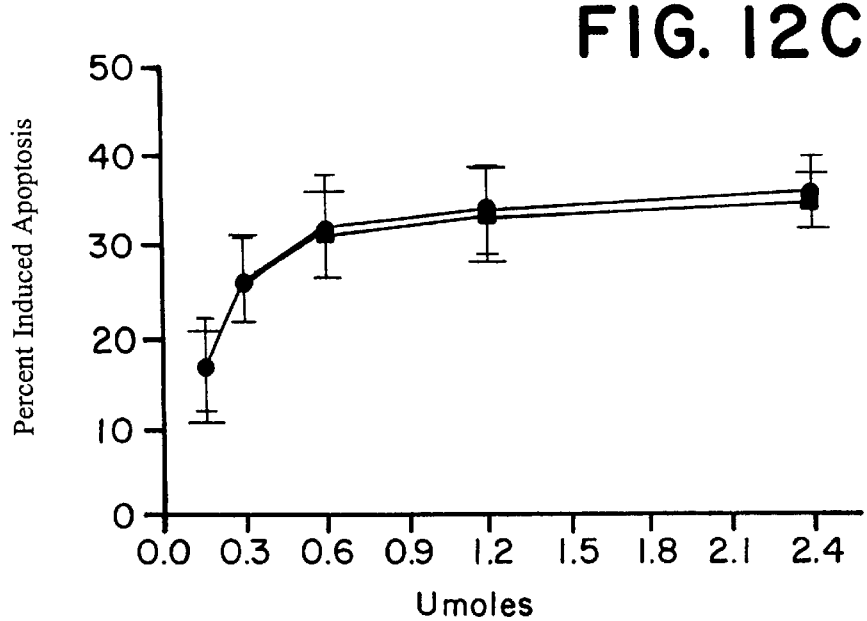

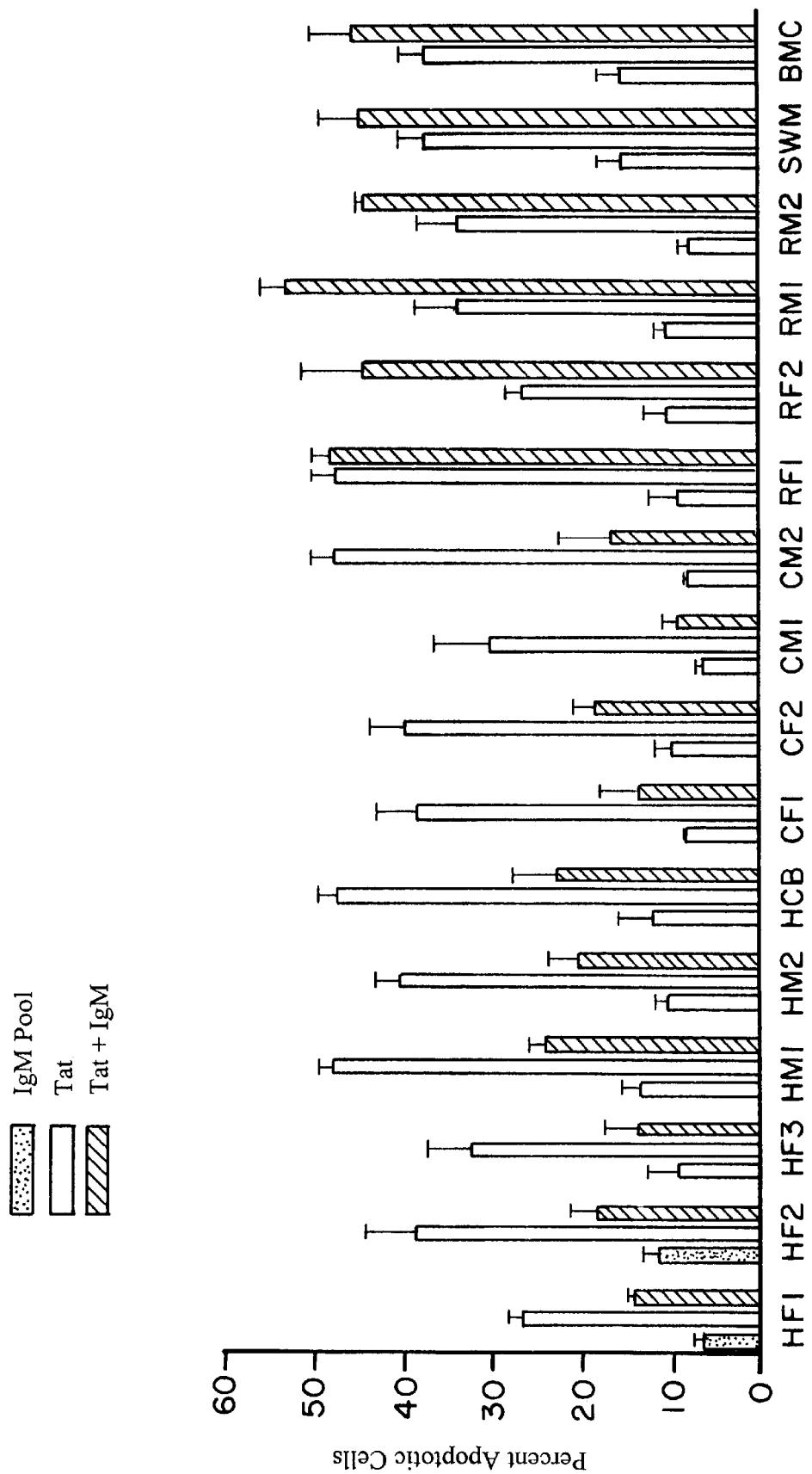

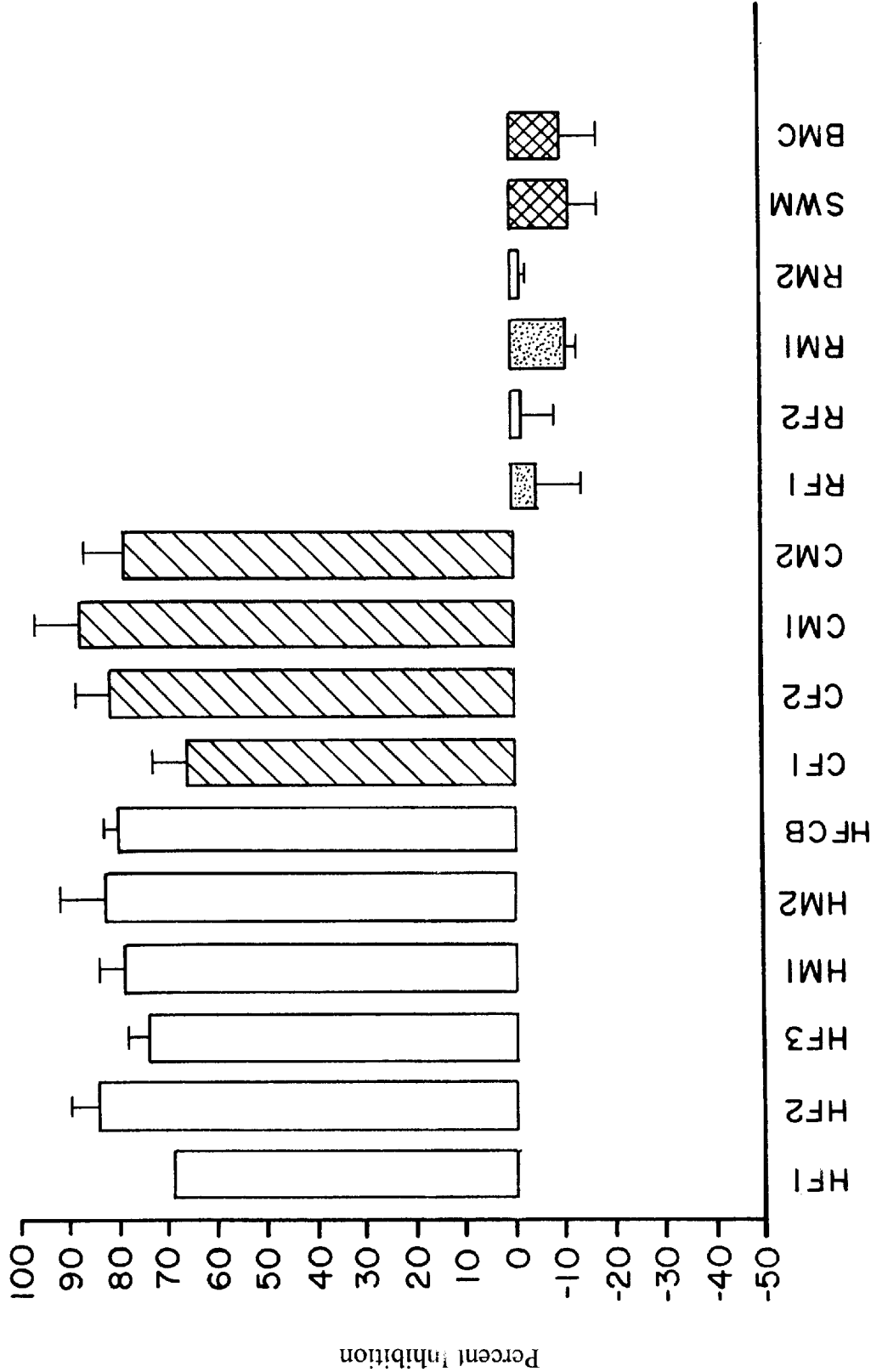

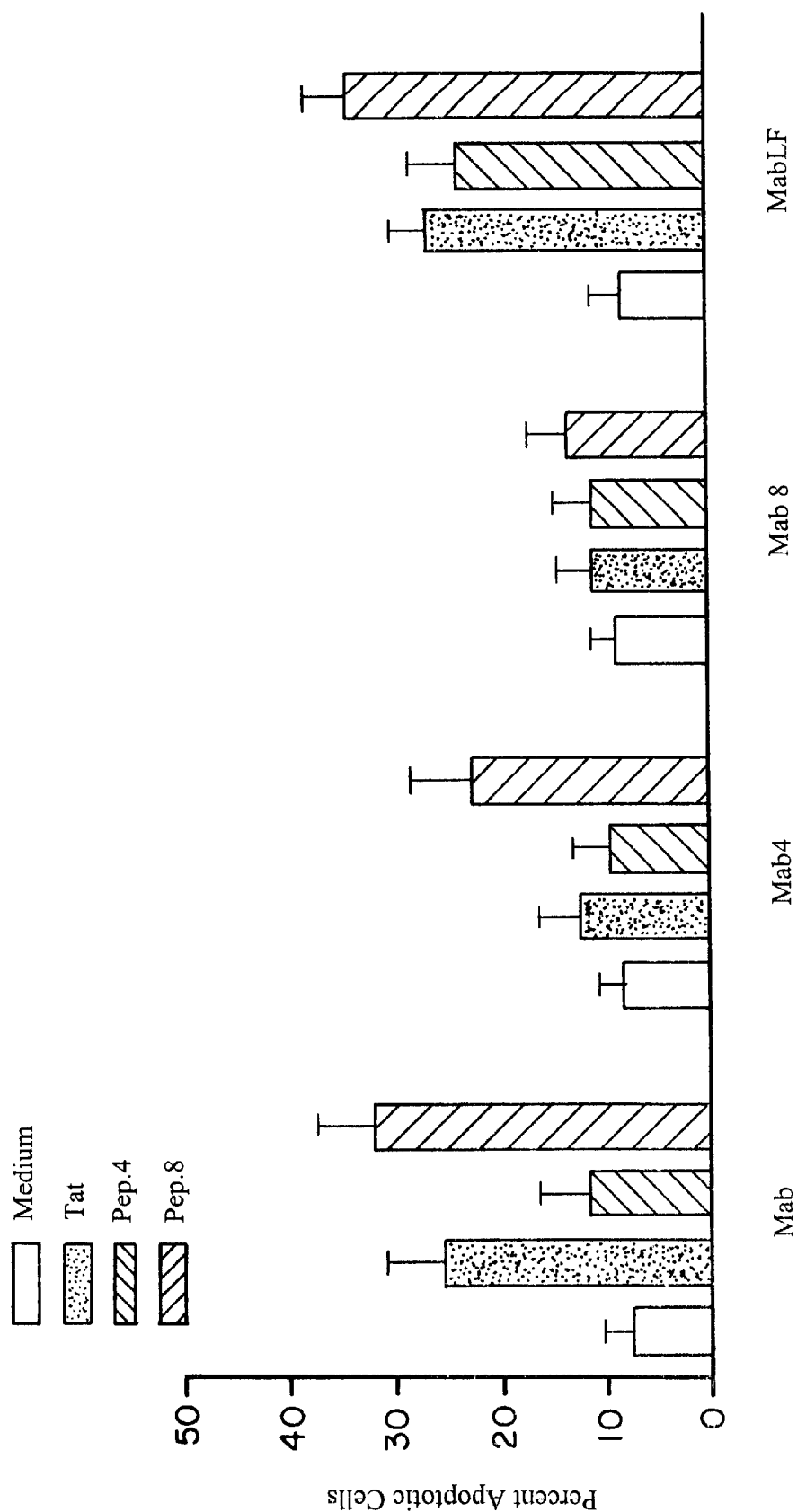

MONOCLONAL HUMAN NATURAL ANTIBODIES

This application is a continuation-in-part application of application Ser. No. 09/198,889 filed Nov. 24, 1998 Now ABN. Ser. No. 09/198,889 claims priority under 35 U.S.C. § 119 from Provisional Application No. 60/066,464 filed Nov. 24, 1997.

BACKGROUND OF THE INVENTION

The effector molecules of the immune system include a repertoire of circulating immunoglobulins non-attributable to exogenous antigenic induction, variously referred to as "autoantibodies" or "natural antibodies". The two terms are not synonymous. Thus, for the "self-attacking" antibodies the term "autoantibodies" is customarily applied, while for the "self-protective" antibodies the term "natural antibodies" is used.

A vast majority of natural antibodies react with one or more "self" antigens. Their importance in immune regulation has long been neglected, since tolerance to "self" was thought to be primarily dependent on the deletion of autoreactive clones, rather than on peripheral suppressive mechanisms. Clonal deletion cannot account, however, for the prevalence of natural autoreactivity among healthy individuals. It is now well established that autoreactive repertoires are predominantly selected early in ontogeny and that autoreactive antibodies, B cells, and T cells, are present in healthy individuals, and in virtually all vertebrate species (Lactoix-Desmazes et al., 1998, J. Immunol. Methods, 216:117–137 and references therein).

Natural antibodies are mostly IgM, polyreactive, and are generally encoded by V genes in germline configuration (Casali et al., 1996, Curr. Top. Microbiol. Immunol., 210:167–79 and references therein). They are mainly produced by B-1 cells which account for most of the B cell repertoire in the fetus and neonate, and possibly play a major role in the development of the adult B cell repertoire.

It is still unclear whether precursors of B-1 cells are capable of undergoing an antigen-driven clonal selection process, thereby producing natural antibodies with a high affinity for the selecting antigen. In this respect, it has been clearly established that B-1 cells can express a hypermutation mechanism similar to that of conventional (B-2) cells and that the main structural correlate for antibody polyreactivity and antigen binding in monoreactive antibodies is provided by the somatically generated CDR3 heavy chain (Casali et al., supra).

Although endowed with self-reactivity, natural antibodies also bind exogenous antigens. Exposure to environmental antigens is not necessary for the emergence of natural antibody-producing cell precursor clones to exogenous antigens, as suggested by the significant population of B cells capable of producing antibodies to a variety of bacterial antigens in germ-free animals (Casali et al., supra). Because of their ability to bind a variety of exogenous antigens, including those on bacteria and viruses, natural antibodies play a major role in the primary line of defense against infections.

U.S. Pat. No. 5,872,012 discloses a circulating natural human antibody immunoreactive with an arginine-rich epitope present on human protamine. U.S. Pat. No. 5,606,026 discloses that the arginine-rich epitope is present in the Tat protein of HIV-1 and further discloses a second circulating human natural antibody immunoreactive with a different epitope on the Tat protein. It has been also shown that these Tat-reactive circulating human natural antibodies decrease after HIV infection reaching minimal levels as the patient progresses to AIDS (Rodman et al., 1999, Hum. Immunol., 60:631–639). In addition, a novel circulating human natural antibody immunoreactive with a cryptic epitope present on human lactoferrin is disclosed therein.

As the correlation of the titers of some of the circulating natural antibodies with disease progression has been established in HIV infection, there is a need in the art to develop new treatment strategies based on supplementing the patient's immune system with effective amounts of exogenously produced natural antibodies. An ideal source of such natural antibodies would be monoclonal counterparts of the circulating human natural antibodies that can be produced in large quantities and used for various therapeutic and diagnostic purposes.

SUMMARY OF THE INVENTION

The present invention provides monoclonal forms of human natural antibodies.

In one aspect, the present invention provides a method for producing human hybridoma cells producing monoclonal human natural antibodies comprising the steps of fusing immortalized or transformed human umbillicord blood cells with mouse: human heteromyeloma cells, isolating fused cells, plating said fused cells under limited dilution conditions, and recovering said hybridoma cells.

In another aspect, the present invention provides human hybridoma cells producing monoclonal human natural antibodies produced by the method of the present invention.

These and other aspects of the present invention will be apparent to those of ordinary skill in the art in light of the present description, claims and drawings.

BRIEF DESCRIPTION OF THE DRAWINGS

FIG. 5. Sequences of the 12 amino acid-long peptides representing the Tat protein of HIV-1. Peptides 1–7 and 9–12 overlap by 5 residues. Peptides containing the arginine-rich region: 7, 8, 9. Peptides containing the cysteine-rich region: 4, 5.

FIGS. 12A, B and C. Induction of apoptosis in human T cells by Tat protein and its constituent peptides. A. Sequences of 12 amino acid-long (overlapping) Tat-derived peptides. B. Analyses of apoptosis induced in T cells of human blood specimens. Each bar represents a mean of 8 analyses in blood specimens collected from each of 6 normal humans. Cells from each donor were tested with Tat protein and each peptide listed in A. The absolute standard range of measurements (SRM) for each bar is indicated. C. Apoptotic response to equivalent molar doses of Tat protein and peptide 8.

FIGS. 13A and B. Control by species-specific IgM pools of Tat-induced apoptosis of human T cells. Each IgM pool was obtained from circulating blood of individual human adult females (HF) and males (HM), a pool of human cord bloods (HCB), individual chimpanzee females (CF) and males (CM), individual rhesus females (RF), and males (RM). The mouse IgM pools were derived from combined blood specimens of male, female and juvenile Swiss Webster mice (SWM) and of Balb C mice (BCM). The tested cells represented groupings of PBL from three or four normal adult humans. Each set of assays was carried out on the same set of substrate cells. A. Determination of percentage of apoptotic cells in the samples. Each bar represents the content of a separate well and the percent of apoptotic cells in that well. B. Determination of percent inhibition in the samples. The Tat inhibition capacity of each IgM pool was assayed a minimum of 3 times, the average calculated and the SRM determined.

DETAILED DESCRIPTION OF THE INVENTION

All patents, patent applications and literature references cited herein are hereby incorporated by reference in their entirety.

Figure 2A:
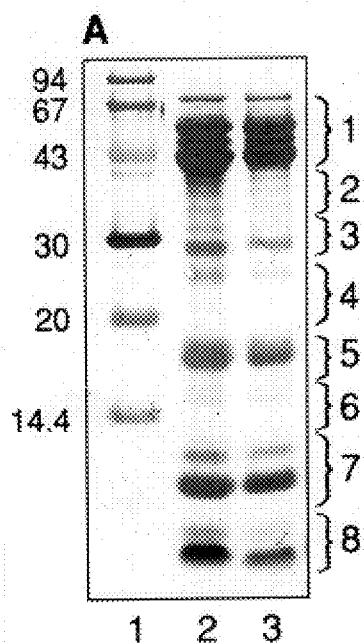
FIGS. 2A, B and C. Tricine-PAGE analysis of cyanogen bromide (CNBr)-mediated cleavage products of milk lactoferrin (LF(M)) and sperm head-derived protein SP80. The lane numbers correspond to: 1- molecular weight markers; 2- LF(M); 3- SP80-basic; 4-SP80-acidic. A. Protein staining showing that fraction 7 contains two distinct bands. B. Immunotransfer with normal human serum showing reactivity specifically localized to fraction 7B. C. Immunotransfer with a monoclonal IgM antibody secreted from a human B cell-derived hybridoma showing reactivity specifically localized to fraction 7B.
Figure 2B:
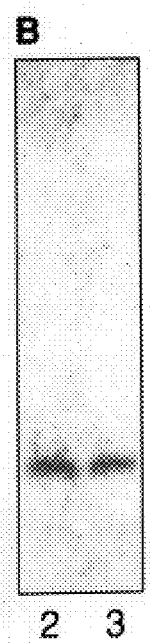
Figure 2C:
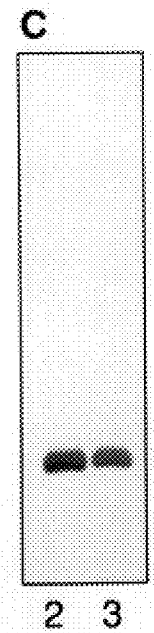
Figure 3A:
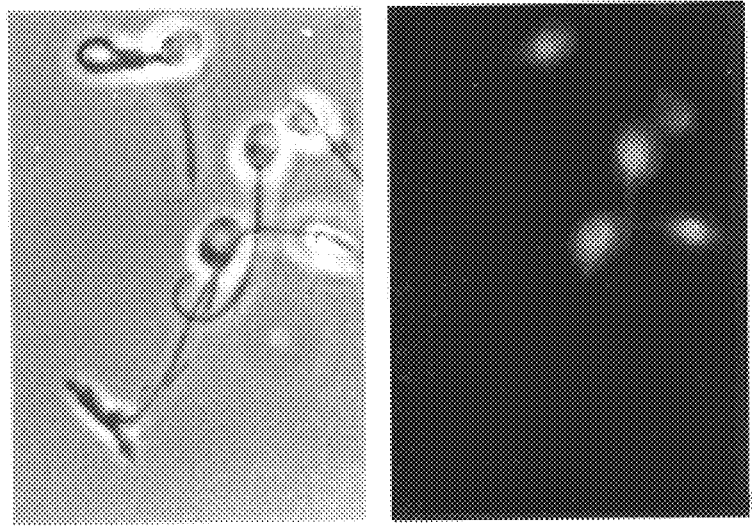
FIGS. 3A and B. Phase-contrast (left) and immunofluorescence (right) analysis of human sperm cells using either human serum (A) or monoclonal IgM antibody reactive with LF fraction 7B (B), and FITC-labeled anti-human IgM (secondary antibodies).
Figure 3B:
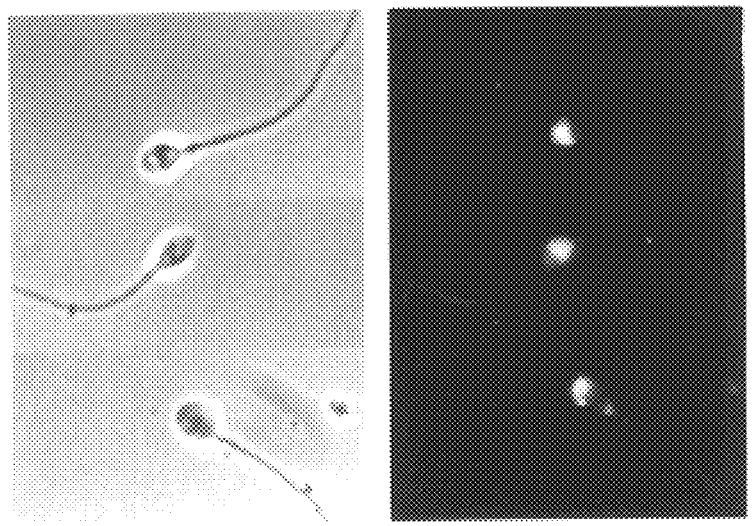

The lactoferrin (LF)-reactive IgM antibody present in a large cohort of human sera represents a natural antibody as it is ubiquitously distributed, has no pathologic role and is not produced in response to a heterologous antigen. The reactive site for this natural antibody has been identified previously (Rodman et al., 1985, Science, 228:1211–1215) and confirmed in the instant invention to be present in the plasma membrane complex of the human sperm head. These studies have confirmed that previously characterized 72.6 kD LF present in seminal plasma (Goodman and Young, 1981, J. Reprod Immunol., 21:99–108), accurately determined here to have a molecular weight of 80 kD, is also present in the protein coat of the sperm head. It is further shown herein that the noted natural antibody specifically recognizes the conformation of LF that is different from its native conformation in body fluids and is revealed in vitro upon its denaturation (FIGS. 2, 4) or in vivo upon its incorporation in the protein coat of the human sperm head (FIG. 3).

Although the mechanism of the drastic conformational change of LF present in the seminal plasma which happens upon its incorporation in the spermatozoal membrane/coat complex is presently unknown, this transition presumably takes place during the period of spermatogenic maturation in the seminiferous tubules of the testes. It is relevant, therefore, to note that large molecules such as immunoglobulins, particularly IgM, are excluded from the lumina of the seminiferous tubules (Haas et al., part 2, Chapter 7, In Reproductive Immunology, Bronson et al., eds., Mass. Blackwell Science., 1996) and, therefore, from immunoreactivity with sperm components during spermiogenesis. That barrier, however, does not exist in the female reproductive tract, where the full complement of circulating antibodies is present (Yee and Silver, part 2, Chapter 33, In Reproductive Immunology, Bronson et al., eds., Mass. Blackwell Science., 1996). Therefore, the LF-reactive natural antibody is available for immunoreactivity with the LF of the sperm coat, following ejaculation into the female reproductive tract. This interaction may take place in the sperm coat in situ (as shown in FIG. 3) or upon the release of LF, along with other coat and plasma membrane components, as the sperm undergoes capacitation and acrosome reaction (FIG. 4), which facilitate passage of the sperm through the protective zona pellucida surrounding the oocyte, and subsequent entry into the oocyte (Yanagimachi, pp.189–317, In The Physiology of Reproduction, Knobil and Neil, eds., Raven Press, New York, 1994; Aitken, p. 2–10, In Scientific Essentials of Reproductive Medicine, Hillier et al., eds. W. B.Saunders, London, 1996). Since the acrosome reaction involves fusion of the acrosomal membrane with the plasma membrane, the components of the overlying protein coat become dispersed. Thus, if it were not for the anti-LF natural antibody activity present in the fertilization milieu, the released LF could have ready access to various components of the ooplasm.

Among the many functions and interactions defined for LF, its capacity to be endocytosed and interact with DNA is of increasing interest (He and Furmanski, 1995, Nature, 373:721–724; Bi et al., 1996, Eur. J. Cell Biol., 69:288–296; Fleet, 1995, Nutr. Rev., 53:226–231; Garre et al., 1992, J. Cell Physiol., 153:477–482; Hutchens et al., 1991, Ped. Res., 29:243–250). Particularly interesting are the recent reports that the interaction of LF with DNA is marked by sequence specificity (He and Furmanski, supra). The underlying molecular bases for that specificity have not been defined, but it is reasonable to expect that if LF/DNA interaction occurs in vivo, it does so within a defined control system. A natural antibody selectively reactive with a conformation of LF incorporated into the sperm coat, but not with its ubiquitous circulating conformation, may play role in such control system by: (1) inhibiting the interaction of LF with the DNA of the fertilized oocyte and (2) restricting the inunuoreaction of the circulating natural antibody with LF at other loci.

In one preferred embodiment, the present invention provides a monoclonal form of a human, natural IgM antibody immunoreactive with a crytic conformational-sensitive epitope present on human LF. This antibody is produced by a hybridoma cell line, RWL-1, which was deposited with the American Type Culture Collection (Manassas, Va.) on Nov. 14, 1997 and received the Accession No. ATCC CRL 12431. The hybridoma was produced by fusing an Epstein-Barr virus (EBV)-transformed human umbilical cord blood B cell with a mouse:human heteromyeloma cell (HMMA) as described in Example 1 below. This hybridoma produces human monoclonal antibodies of the IgM isotype. The fact that the antibody-producing cell (the human umbilical cord cell) is of neonate origin and the antibody is of the IgM isotype (and therefore does not cross the placenta) demonstrates that the disclosed monoclonal antibodies are true counterparts of the natural antibody.

As shown below in Example 2, said monoclonal antibody is immunoreactive with an epitope present on SP80, the 80 kD glycosylated homolog of LF which is localized in the protein coat of the sperm head. As mentioned above, following the induction of the acrosome reaction occurring during fertilization, LF could potentially interfere with the interaction of sperm and oocyte DNA. Therefore, one of the uses of the monoclonal antibodies of the present invention is as an additive to in vitro fertilization reactions in order to prevent LF from interacting with sperm DNA prior to fertilization.

In alternative, preferred embodiments of the present invention, hybridoma cells producing monoclonal IgM antibodies immunoreactive with the Tat protein of HIV-1 are provided. These hybridoma cell lines, RWT-4 and RWT-12, are immunoreactive with Tat-derived peptide 4 and peptide 8, respectively (see peptide sequences in FIG. 5). These hybridoma cells, as is the case with hybridoma RWL-1, were produced by fusing EBV-transformed human umbilical cord blood B cells with HMMA cells. RWT-4 cells were deposited with the ATCC on Feb. 12, 1998 and received the Accession No. ATCC CRL 12472, and RWT-12 cells were deposited on Feb. 25, 1998 and received the Accession No. ATCC CRL 12477. The detailed characterization of anti-Tat monoclonal antibodies produced by these hybridomas is provided below in Example 3.

The Tat-reactive monoclonal antibodies of the instant invention are produced by hybridomas of neonate origin and belong to IgM isotype. Therefore, these antibodies are the monoclonal equivalents of the circulating IgM natural antibodies described in U.S. Pat. No. 5,606,026.

Comparison of cohorts of HIV+ and normal (HIV–) sera performed in the present invention (see Example 4 below) indicate that, following a period of post-infection latency, the titers of those natural antibodies decline and other Tat-reactive antibodies do not arise.

It is further disclosed herein that the human-specific pattern of innate/adaptive reactivity with HWV-1 Tat protein is shared by chimpanzees, but not by other mammals, in which those natural antibodies are not present, and the induced Tat-reactive antibodies do arise.

The data disclosed in Example 4 (FIGS. 9, 10 and 11) clearly establish a correspondence, in HIV+ humans, between the CD4+ T cell count and the serum titer of the two Tat-reactive IgM natural antibodies, specifically with the antibodies which interact with the epitopes represented by Tat-derived cysteine-rich peptide 4 and by arginine-rich peptide 8 (see peptide sequences in FIG. 5). A temporal relationship between the decline of the Tat-reactive natural antibodies and the demise of CD4+ T cells, suggests a role for these antibodies in retardation of the pathoprogression of HIV infection. This role is consistent with the important function of Tat protein in mediating viral internalization, viral replication, and virus-induced host-cell apoptosis (see Examples 4, 5 below). In fact, Example 5 of the present invention provides experimental evidence that both natural anti-Tat IgM antibodies and their monoclonal counterparts specifically inhibit Tat-induced T cell apoptosis. As disclosed in Example 5, the interference with Tat-induced apoptosis of human T cells is shared by chimpanzee IgM pools, but not by IgM pools of rhesus macaques or of mice. These observations provide evidence for a role of species-specific innate immune factors in disease control and introduce a new pathway for development of HIV treatment modalities.

It should be noted, however, that during HIV infection, the protective function of the Tat-reactive natural antibodies is evidently limited by the immune system recognition of the natural antibody-reactive sequences of Tat as "self" with consequent induction of tolerance and restriction of production of those antibodies (see also Rodman et al., supra). The limited occurrence of progression to AIDS in chimpanzees may reflect an additional innate characteristic which may be shared by the occasionally observed HIV+ humans who are HIV-1 positive but who do not exhibit any symptoms of the disease and are known as long-term survivors (LTS) or long-term-non-progressors (LTNP).

As the circulating Tat-reactive natural antibodies are deficient in HIV-infected individuals and decrease as AIDS approaches, the present invention discloses the assay for prognosing the onset of AIDS which is based on determining the titer of these antibodies in patients' serum.

Another preferred embodiment of the invention is a method for treating a patient suffering from an HIV-1 infection comprising administering an effective amount of natural human IgM antibodies selected from a group consisting of antibodies produced by RWT-4 cells, antibodies produced by RWT-12 cells and mixtures thereof. It is envisioned that the replenishment of the natural antibodies deficient in HIV-1-infected and AIDS patients will be of clinical benefit to these individuals in light of the arguments presented above and for the following additional reasons:

a) as shown below in Example 4, the Tat protein of HIV-1 does not stimulate the induction of antibodies in humans (see Table IV);

b) long-term survivors (LTS)/long-term non-progressors (LTNP) have normal levels of the circulating Tat-reactive natural antibodies.

In yet another preferred embodiment of the present invention, a method for increasing CD4+ T cell counts in a patient is provided comprising administering to a patient in need of such treatment an effective amount of antibodies selected from the group consisting of antibodies produced by RWT-4 hybridoma, RWT-12 hybridoma and mixtures thereof.

The instant invention further provides an in vitro method to determine the protective effect and the effective dose of pharmaceutically administered anti-Tat antibodies (e.g., monoclonal counterparts of the natural IgM antibodies). Said method is based on measuring the extent of antibody-mediated inhibition of Tat-induced T cell apoptosis (see Example 5 below).

The monoclonal IgM antibodies produced by hybridomas of the present invention can be isolated from cultures of the cells that produce them and purified using conventional techniques known to those of ordinary skill in the art, such as ammonium sulfate precipitation, HPLC column chromatography, etc.

The pharmaceutical dosage administered will vary depending upon known factors such as age, health and weight of the recipient, type of concurrent treatment, frequency of treatment, etc. Usually, a dosage of active ingredient is between 0.001 and 10 milligrams per kilogram of body weight. Precise dosage, frequency of administration and time span of treatment should be monitored, for each individual, by determination of clinical indications of relief from the disease progression (e.g., rise in CD4+ T cell count).

For parenteral administration, the antibodies of the present invention can be formulated into pharmaceutical formulations or dosage forms as a solution, suspension, emulsion, or lyophilized powder in association with a pharmaceutically acceptable vehicle. Examples of such vehicles are water, saline, Ringer's solution, dextrose and 5% human serum albumin. In addition, various Intravenous IgG (IVIG) preparations are currently commercially available (e.g., from Sandoz Pharmaceuticals or Cutter Biological) and have been tested and certified for parenteral administration. These IVIG preparations have been reported to provide beneficial effects in treatment of a large number of autoimmune diseases (Lacroix-Desmazes et al., 1996, Clin. Exp. Rheumatol., Suppl. 15: S9–15) and can be used as vehicles for delivery of the antibodies of the present invention.

Each pharmaceutical formulation of the present inventions does not need to contain an effective amount of the antibodies since such amounts can be achieved by administering a plurality of such formulations.

In addition, as disclosed in Gore, M. M. et al (*Human Antibodies*, 1997 Vol. 8,1) when using monoclonal antibodies produced by hybridomas generated by fusing Epstein Barr Virus (EBV—transformed human B cells with appropriate fusion partners, contaminating EBV DNA can pose a problem. However, EBV can be omitted if the B cells (or in this case, umbillicord blood cells) are trated with the non-transforming mitogen formalized *Staphyloccus aures*, commercially available from Sigma chemical company (St. Louis, Mo.). This preferred embodiment of the present invention is detailed in Example 6 below.

EXAMPLES

The present invention will be better understood by reference to the following Examples, which are provided by way of exemplification and not by way of limitation.

Example 1

Production of RWL-1 Hybridoma Cell Line

The hybridoma, RWL-1, which secretes the monoclonal human IgM antibody reactive with a defined cryptic sequence of human lactoferrin (LF), was created by fusion of a human umbilical cord blood B cell with the human-:mouse heteromyeloma cell line (HMMA; Posner et al., 1987, Hybridoma, 6:611) as set forth below.

The cord blood was obtained, at caesarian section, from a normal (but otherwise non-identified) neonate and mononuclear cells were isolated by density gradient centrifugation using FICOLL-PAQUE® (Pharmacia).

Selected cultures of EBV-immortalized B cells were grown to a cell density of $10^6$ cells/well, then washed 5 times in RPMI 1640 (non-supplemented). The fusion partner (HMMA cells, described in Posner et al., supra) was grown in RPMI 1640, FCS, Pen/Strep and azaguanine, and washed 3 times in non-supplemented RPMI 1640. $10^6$ cells were mixed with an equal number of the EBV-immortalized cells. The mixed cell culture was pelleted, supernatant decanted and the cells resuspended in warm (37° C.) 40% polyethylene glycol/RPMI 1640 (pH 7.2) and held for one minute. The cells were again pelleted, washed 2 times with RPMI, pH 7.8, then resuspended ($10^6$ cells/ml) in HY medium (Sigma), supplemented with 20% FCS, HAT (Sigma), ouabain, Pen/Strep and plated out at a density of $10^5$ cells/well. After 3 weeks, the wells containing growing cells were tested for the production of a specific antibody. The contents of the antibody-positive wells were diluted and replated at a density of 0.5 cells/well (to insure monoclonality) in HY/HT medium (Sigma) supplemented with 20% FCS, SPIT (Sigma), Pen/Strep. The cells were grown for 5 weeks (37° C.) and the contents of each well were retested for Mab specificity. Selected cultures were grown to a density of $10^6$ cells/ml and spun at 400 RPM, 5 min. Each cell pellet was resuspended in 5 mil of 80% FCS, 10% DMSO and 10% RPMI 1640 and stored frozen at −70° C., in 2 ml aliquots. A few of the stored aliquots were defrosted and retested for viability and antibody specificity.

The hybridoma was deposited on Nov. 14, 1997 with the American Type Culture Collection (Rockville, Md.) and received the Accession No. ATCC CRL 12431.

Example 2

Identification of the Cryptic Epitope of LF Reactive with the Natural Antibodies Materials and Methods LF proteins Human milk lactoferrin, LF (M), was obtained from Sigma (L3770). Seminal plasma LF, SP80, was isolated from pooled specimens of semen from clinically normal volunteer donors. Following liquefaction, sperm-free plasma was obtained by centrifugation and separated by DEAE ion-exchange chromatography (Friesen et al., 1981, J. Applied Biochem., 3:164–175) into a pool of basic and a pool of acidic fractions. Each pool was subjected to gel filtration (SEPHACRYL™ S 300 HR, Pharmacia) and the first fraction of each pool corresponding to 80 kD molecular weight was isolated and designated SP80-basic and SP80-acidic, respectively.

Figure 1A:
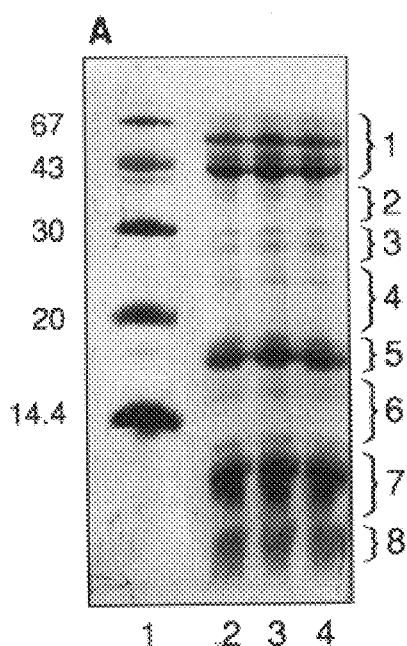
FIGS. 1A, B and C. SDS-PAGE analysis of cyanogen bromide (CNBr)-mediated cleavage products of milk lactoferrin (LF(M)) and sperm head-derived protein SP80. The lane numbers correspond to: 1- molecular weight markers; 2- LF(M); 3- SP80-basic; 4-SP80-acidic. A. Protein staining showing identical CNBr cleavage pattern (fractions 1–8) of all three proteins. B. Immunotransfer with serum of rabbit immunized with SP80 (acidic and basic) showing multiplicity of reactive sites and homology of reactivity of LF(M) and SP80. C. Immunotransfer with normal human serum showing reactivity solely with fraction 7 in the cleavage pattern of each of the proteins.

Cyanogen bromide (CNBr) cleavage and SDS-PAGE analysis of the LF cleavage products CNBr treatment of SP80-basic, SP80-acidic and LF(M) was carried out as described (Metz-Boutigue et al., 1984, Eur. J. Biochem., 145:659–676). Briefly, a 10 mg/ml 70% formic acid solution of each protein was incubated with CNBr (200-fold molar excess) at room temperature for 18–24 hr. Following lyophilization, the cleavage mixtures were electrophoresed on an SDS-PAGE (FIG. 1A) or on a 16.5% Tricine gel (Schagger and van Jagow, 1987, Anal. Biochem., 166:368–373) for enhanced resolution of the low molecular weight fractions (FIG. 2).

Immunoreactivity of CNBr cleavage products of LF

Western blot was performed on Immobilon-P (Millipore) transfers of the electropheretograms of LF(M) and acidic and basic SP80 and visualized by chemiluminescence. ELISA was carried out according to standardized methodology (Rodman et al., 1988, J. Exp. Med., 167:1228–1246; Pruslin et al., supra; Rodman et al., 1993, Proc. Natl. Acad. Sci. USA, 90:7719–7723). All assays were performed using serum of a rabbit immunized with human LF(M), serum of a rabbit immunized with SP80 (acidic and basic combined) and control pool of normal human sera.

Production of monoclonal antibodies specific for fraction 7B

Mononuclear cells were isolated from cord blood of a normal neonate by density gradient centrifugation using FICOLL-PAQUE® (Pharmacia) and transformed with EBV (Chiorazzi et al, 1982, J. Exp. Med., 156:930–935). Fusion of EBV-transformed cells with the HMMA cell line was performed utilizing standard procedures (Chiorazzi, 1992, Mol. Biol. Reports, 16:65–73) and resulted in a set of IgM-secreting hybridomas for which monoclonality was established by limiting dilution. Since reactivity of serum with denatured LF(M) and SP80 was confined to a single Tricine PAGE fraction (fraction 7B; FIG. 2), that fraction was isolated from the gel and utilized as antigens in ELISA assays to screen for those monoclonal antibodies that possess exclusive reactivity with the fraction 7B.

Characterization of fraction 7B

Fraction 7B was excised from the gel and extracted with $H_2O$. SDS was precipitated by the addition of KCl, and the component peptides of the fraction were dialyzed against PBS (pH 7.2). Determination of the molecular weight and the number of the peptides constituting purified fraction 7B was carried out at the Laboratory of Mass Spectrometry at Rockefeller University, utilizing matrix-associated laser desorption/ionization mass spectrometry (Beavis and Chait, 1990, Anal. Chem., 62:1836–1840). N-terminal sequencing of the two identified peptides was carried out at the Protein Sequencing Facility at Rockefeller University, utilizing repeated cycles of Edman degradation followed by PTH analysis with microbore HPLC (Atherton et al., pp. 409–418; In *Techniques in Protein Chemistry IV*, Angeletti, ed., Calif. Academic Press., 1993).

Cytologic localization of LF/SP80 in sperm heads

A fraction of swim-up human sperm was obtained from spontaneously liquefied seminal plasma, fixed, washed 3 times with PBS, and suspended in either human serum diluted 1:500 in PBS or in PBS solution containing purified monoclonal antibodies, followed by overnight incubation at 40° C. Each suspension was washed 3 times with PBS, and collected sperm incubated with FITC-labeled secondary antibodies (anti-human IgM; Sigma) for 1 hour. The sperm were washed with PBS, and a drop of the suspension placed on a slide, examined under the microscope and photographed, utilizing FITC-specific filters (FIG. 3).

Purification of sperm coat protein fraction

A fraction containing the components of the sperm coat was obtained by induction of an acrosome reaction (Jamil and White, 1981, Arch. Androl., 7:293–292) in a suspension of spermatozoa: the swim-up sperm were gently washed with PBS, collected, suspended in Ca medium (2 mM $CaCl_2$ 10 mM ionophore A23187 [Calbiochem], 1 mM PMSF [Sigma]) and incubated for 4 hours at room temperature. The sperm cells were then pelleted by low speed centrifugation and the resultant supernatant cleared of particles by high speed centrifugation followed by an overnight dialysis at 40° C. The supernatant (at 10 μg/ml) was tested by ELISA, for reactivity with human sera (diluted 1:100) and with the monoclonal antibodies reactive with LF CNBr cleavage fraction 7B (FIG. 4A). Control reactions were performed using 10 μg/ml of purified fraction 7B LF(M) or 10 μg/ml of native (non-denatured) LF(M) (FIGS. 4B, C).

Results and Discussion

The data reported here confirm previous studies indicating that an 80 kD protein of human seminal plasma, SP80, is homologous with lactoferrin, LF (Hekman and Rumke, 1969, Protides Biol. Fluids, 16:549–552; Goodman and Young, supra). Fractionation of sperm-free seminal plasma by DEAE ion-exchange chromatography confirmed that the 80 kD protein is present in two forms: basic and acidic, the latter containing a glycan moiety (Spik et al., 1994, Adv. Exp. Med. Biol., 357:21–32). The patterns of CNBr cleavage (as analyzed by SDS-PAGE) were identical for both forms of SP80 as well as for LF from human milk, LF(M) (FIGS. 1A and 2A). Also identical were the patterns of immunoreactivity of those CNBr cleavage fractions with serum of a rabbit immunized with SP80 (FIG. 1) or with serum of a rabbit immunized with LF(M) (not shown). The homology of LF and SP80 was further confirmed by the absence of the immunoreactivity of the normal human sera with both native LF(M) and SP80 isolated from, or in the context of, seminal plasma (FIG. 4; see also Manchester et al., 1997, Ann. N.Y. Acad. Sci., 815:475–7). In contrast, all human sera tested was reactive with the single distinct band (fraction 7B) of the SDS-/Tricine-PAGE pattern of CNBr cleavage products of LF(M) and SP80 (FIGS. 1, 2).

Figure 1B:
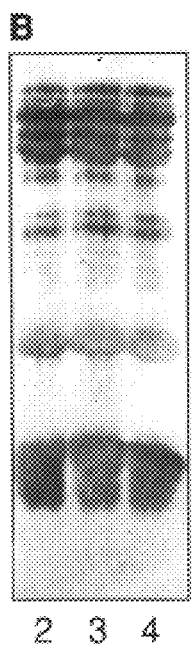
Figure 1C:
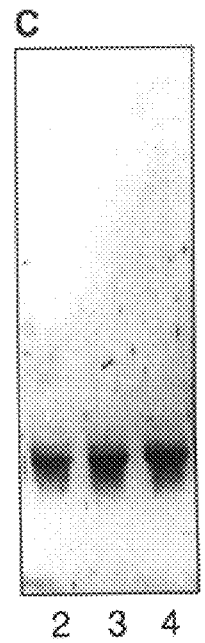
Figure 4:
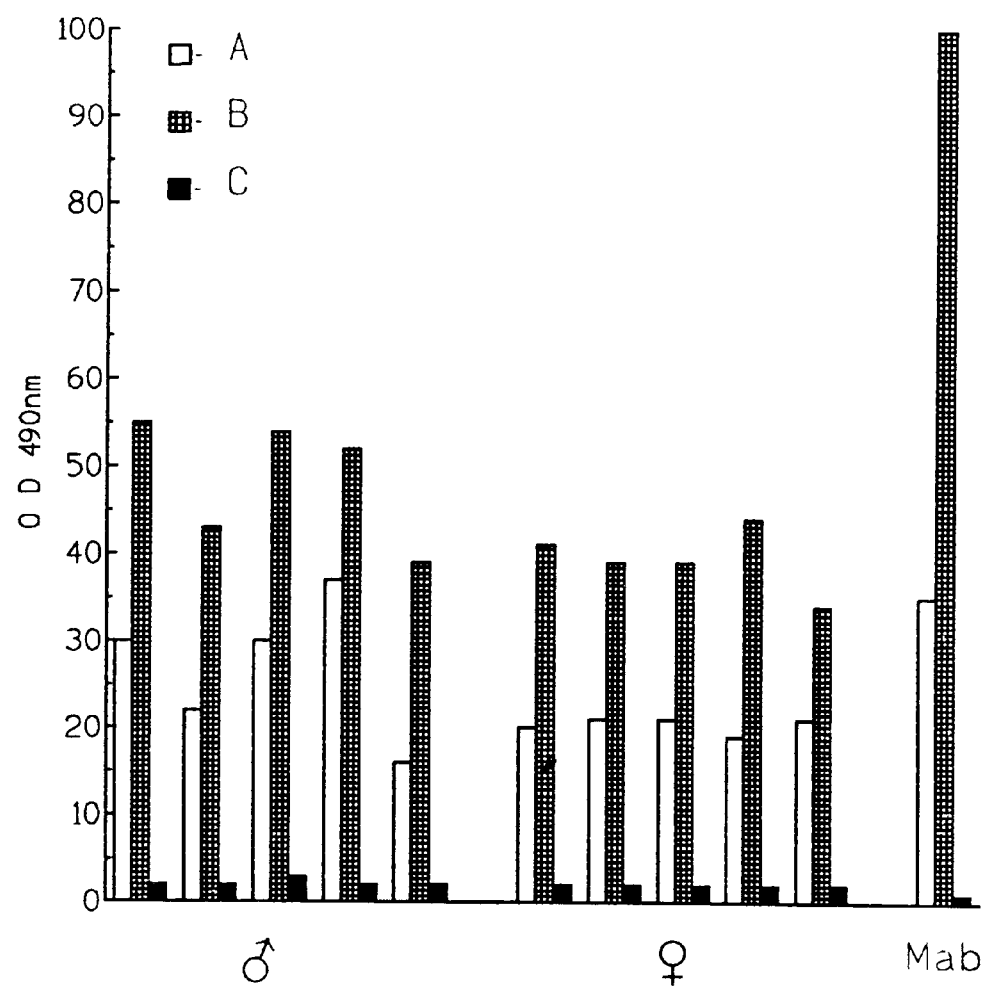
FIGS. 4A, B and C. ELISA assays of 10 different samples of human serum or the monoclonal IgM antibody reactive with LF fraction 7B (Mab) with: (A) the complement of sperm coat proteins released following induction of the acrosome reaction in a suspension of swim-up spermatozoa; (B) purified fraction 7B LF(M); (C) native (non-denatured) LF(M).

Taken together, the absence of the immunoreactivity of native LF(M) and SF80 proteins and the reactivity of denatured peptides derived from these proteins with natural antibodies in normal human sera indicate that said natural antibodies recognize a cryptic sequence of LF that is revealed upon denaturation (FIGS. 1 and 2). As further defined in the present invention, this cryptic sequence is segregated in fraction 7B from the Tricine-PAGE analysis of CNBr cleavage products of LF(M) and SP80 (FIG. 2). The instant disclosure of a human cord blood B cell-derived hybridoma secreting IgM which is specifically reactive with a component of fraction 7B (i.e., RWL-1 cell line) have both confirmed the innate occurrence of the natural anti-LF antibodies and allowed the precise mapping of the cryptic epitope (FIGS. 2 and 4).

Analysis of the fraction 7B by Mass Spectrometry revealed it contains 2 peptides, having molecular weight of 10 kD and 9 kD, respectively. The N-terminal sequencing identified DKVER (amino acid positions 1–5 of SEQ ID NO.:1 ) for the load major peptide and SLDGG (amino acid positions 1–5 of SEQ ID NO.:15) for the 9 kD peptide. Upon the assumption that CNBr cleavage of LF is at methionine residues and by reference to the published structure of LF (Metz-Boutigue et al., supra) the sequence of each of the 2 peptides was localized to the C-terminal lobe of the full-length protein. To further define the immunogenic epitopes, we have created a set of 12-residue-long peptides (with 5-residue-long overlaps) spanning the sequence of the two original peptides (Table I). Thus far, specific reactivity of human serum IgM has not been demonstrated with any one of those peptides tested singly, indicating that the fundamental epitope for the natural antibody, although embodied in LF fraction 7B, is conformation-dependent.

The existence of this conformation-sensitive epitope in vivo is demonstrated in the present invention by cyto-immunoreactivity of human serum containing natural anti-LF antibodies with the sperm head (FIG. 3) and by the ability to produce monoclonal antibodies specifically reactive with LF(M)/SP80 fraction 7B (FIG. 2). As demonstrated herein, this cryptic epitope becomes exposed upon the induction of the acrosome reaction which results in dispersion of the protein coat/plasma membrane ensemble overlying the acrosomal region of the sperm head and produces a component that is reactive with human serum IgM and with the fraction 7B-reactive monoclonal antibodies (FIG. 4). It can be further hypothesized that, upon acrosome reaction in vivo, natural anti-LF antibodies present in the female reproductive tract (Yee and Silver, supra) can prevent the LF (shed from the sperm coat) from interaction with various components of the sperm-penetrated oocyte (e.g., DNA).

TABLE I

Overlapping Duodecapeptides Comprising the Components of LF Fraction 7B

| A. | Seq. ID No: | B. | Seq. ID No: |
|---|---|---|---|
| DKVERLKQVLLH | 1 | SLDGGYVYTACK | 15 |
| KQVLLHQQAKFG | 2 | VYTACKCGLVPV | 16 |
| QQAKFGRNGSDC | 3 | CGLVPVLAENYK | 17 |
| RNGSDCPDKFCL | 4 | LAENYKSQQSSD | 18 |
| PDKFCLFQSETK | 5 | SQQSSDPDPNCV | 19 |
| FQSETKNLLFND | 6 | PDPNCVDRPVEG | 20 |
| NLLFNDNTECLA | 7 | DRPVEGYLAVAV | 21 |
| NTECLARLHGKT | 8 | YLAVAVVRRSDT | 22 |
| RLHGKTTYEKYL | 9 | VRRSDTSLTWNS | 23 |
| TYEKYLGPQYVA | 10 | SLTWNSVKGKKS | 24 |
| GPQYVAGITNLK | 11 | | |
| GITNLKKCSTSP | 12 | | |

TABLE I-continued

Overlapping Duodecapeptides Comprising the Components of LF Fraction 7B

| A. | Seq. ID No: | B. | Seq. ID No: |
|---|---|---|---|
| KCSTSPLLEACE | 13 | | |
| SPLLEACEFLRK | 14 | | |

A. 10 kD peptide;
B. 9 kD peptide

Example 3

Production of RWT-4 and RWT-12 Hybridoma Cell Lines Secreting Anti-Tat Monoclonal Antibodies; Testing of Antibody Reactivity Materials and Methods Production of hybridomas For each hybridoma human umbical cord blood B cells were obtained and immortalized by transformation with EBV as described in Example 1.

After growing for five weeks, the culture medium of each EBV-transformed cell line was tested by ELISA for reactivity with HIV-1 Tat protein and with each of the Tat-derived peptides shown in FIG. 5. Three of those cultures displayed reactivity only with peptide 4 (and at lower levels with peptide 5) and three displayed reactivity only with peptide 8 (and at lower level with peptides 7, 9). All six cultures were selected for fusion with the respective fusion partner.

Hybridomas were prepared by fusion of an EBV-transformed human umbilical cord blood B cell with a heteromyeloma as described in Example 1. A heteromyeloma fusion partner for RWT-4 hybridoma was SHM-D33 HMMA obtained from ATCC (Accession No. ATCC CRL 1668). A heteromyeloma fusion partner for RWT-12 hybridoma was HMMA described by Posner et al. (supra).

The hybridomas were grown to a cell density of $10^6$ cells/ml in NY/HT medium (Sigma), supplemented with 20% fetal calf serum, SPIT (Sigma) and Pen/Strep, and spun at 400 RPM for 5 min. Each pellet was resuspended in a medium containing 80% fetal calf serum, 10% DMSO and 10% RPMI 1640, and stored, in 2 ml aliquots, at −70° C. or in liquid nitrogen. The aliquots representing the hybridomas RWT-4 and RWT-12 were deposited with ATCC on Feb. 12, 1998 and Feb. 25, 1998, respectively. They have received the Accession Nos. ATCC CRL 12472 (RWL-4) and ATCC CRL 12477 (RWL-12).

Purification of hybridoma-derived monoclonal antibodies and their class determination Monoclonal antibodies were recovered from the culture medium of each hybridoma using the following procedure:

a) the medium was concentrated in a centricon C-100 column to remove salt and all proteins of molecular weight less than 100 kD;

b) the concentrated medium was then passed through a size-exclusion gel on a Pharmacia S-300 column;

c) the first protein peak was collected and its purity was analyzed by SDS-PAGE;

d) the remaining portion of the peak was reconcentrated in a new centricon C-100 column to a concentration of 200 $\mu$g/ml and stored.

As judged by the two-band pattern on SDS-PAGE (corresponding to light and heavy immunoglobulin chains), the resulting protein preparation contained pure IgM monoclonal antibodies.

The identity of the light chain of each monoclonal antibody was further verified by ELISA assays using peroxidase labelled anti-gamma and anti-kappa antibodies.

TABLE II

Light Chain Identification

ELISA
1. unlabeled rabbit > IgM
2. Monoclonal antibodies were recovered from the culture medium of each hybridoma using the following procedure:
   a) the medium was concentrated in a CENTRICON ®C-100 column to remove salt and all proteins of molecular weight less than 100 kD;
   b) the concentrated medium was then passed through a size-exclusion gel on a Pharmacia S-300 column;
3. peroxidase labeled anti-kappa or anti-lamda antibodies

|  | 0 ab | Total IgM | RWT-4 Mab |
|---|---|---|---|
| Anti-Lambda | | | |
| 1:4k | 01 | .24 | .73 |
| 1:6k | 01 | .16 | .54 |
| 1:10k | 0 | .12 | .37 |
| Anti-Kappa | | | |
| 1:4k | 04 | .55 | .06 |
| 1:6k | 01 | .36 | .04 |
| 1:10k | 0 | .23 | .02 |

Conclusion: light chain for RWT-4 is lambda.

|  | 0 ab | Total IgM | RWT-12 Mab |
|---|---|---|---|
| Anti-Lambda | | | |
| 1:4k | 02 | .89 | .03 |
| 1:6k | 01 | .65 | .02 |
| 1:10k | 07 | .45 | .01 |
| Anti-Kappa | | | |
| 1:4k | 04 | >1.00 | .80 |
| 1:6k | 03 | .83 | .57 |
| 1:10k | 02 | .56 | .39 |

Conclusion: light chain for RWT-12 is kappa.

The epitope specificity of each monoclonal antibody was identified in ELISA assys using a set of Tat-derived peptides (see peptide sequences in FIG. 5). ST (standard serum) was used as 1:100 dilution. For assays with monoclonal antibodies, the diluted hybridoma cell culture medium (1 $\mu$l/ml) was used.

TABLE III

Epitope Determination in Terms of Tat Peptide Specificity

| Tat Peptide No. | ST | RWT-4 Mab | RWT-12 Mab |
|---|---|---|---|
| 1 | .01 | .03 | .05 |
| 2 | .02 | .02 | .04 |
| 3 | .03 | .01 | 0 |
| 4 | .48 | .94 | .02 |
| 5 | .20 | .35 | .12 |
| 6 | .07 | .01 | .07 |
| 7 | .16 | .07 | .36 |
| 8 | .33 | .16 | .72 |
| 9 | .12 | .07 | .42 |
| 10 | 0 | .02 | .01 |
| 11 | 0 | .01 | .03 |
| 12 | 0 | 0 | 0 |
| Total Tat Protein | .49 | .55 | .44 |

The ELISA data presented in Tables II and III represent an average, for each antibody/antigen reaction, of 20 separately run assays.

Example 4

Analysis of Epitope- and Species-Specificity of Natural Anti-Tat Antibodies; Investigation of the Correlation of Natural Anti-Tat Antibody Titers and the Pathoprogression of HIV-1 Infection Materials and Methods Antigens Recombinant Tat protein was obtained in lyophylized form from Intracel Corp. Reactivity and working dilution for each vial of the protein was standardized with a single standard human serum (Rodman et al., 1997, Human Immunol., 55:87). Tat peptides (FIG. 5), representing overlapping sequences in accordance with the published amino acid alignment of HIV-1 Tat (Frankel et al., 1989, Proc. Natl. Acad. Sci. USA, 86:7397) were prepared as previously described (Rodman et al., 1992, J. Exp. Med., 175:1247).

Sera

Human

In experiments reported in FIG. 6, 70 HIV+ and 70 HIV− human sera were tested. HIV+ sera were collected prior to 1994 to assure that their characteristics are not attributable to the anti-HIV medications in use since that time. In experiments reported in FIGS. 9–11, sera for the HIV+ serial sets were derived from specimens submitted for clinical examination with clinical data and concurrent medication noted. For all experiments, the normal (HIV−) sera were assembled from specimens submitted for pre-employment examination identified only by age, gender and "no clinical findings", and from donations by laboratory personnel. All sera were assayed for reactivity with HIV-1 Tat protein and Tat-derived synthetic peptides.

Chimpanzees

A total of 22 sera from adult chimpanzees, certified as normal, were obtained: 16 (7♂, 9 ♀) from YERKES Regional Primate Center, Emory University; 6 (2♂, 4 ♀) from LEMSIP, NYU Medical Center. Serum of 1 ♂ and 1 ♀ of the latter group were collected 10 and 22 months post-innoculation with HIV-infected cells.

Monkeys

A total of 32 sera from normal monkeys were obtained: 20 rhesus macaques from YERKES, 1 from LEMSIP and 2 from LARC, Rockefeller University; 4 pig tail macaques and 5 baboons from LARC. Also, serum was obtained from 1 of the rhesus macaques following innoculation with SIV (Mac 239)-infected cells. Two additional specimens of rhesus plasma, 6 months post-innoculation with cell-free supernatant of SIV Mac 239 culture, were obtained from Aaron Diamond AIDS Research Center, Rockefeller University.

Rabbits

Sera were obtained from 30 (15 ♂, 15 ♀) New Zealand white rabbits prior to any treatment (sources: LARC; Hospital for Special Surgery, New York). One specimen of rabbit serum post-immunization with HIV-1 Tat protein was obtained from Intracel Corp. (Isaquah, Wash.).

Mice

Sera from 30 normal adult mice (12 Balb C, 6 C57 black, 2 MRL-lpr, and 10 Swiss Webster) were obtained from LARC. A series of 3 immunizations with HIV Tat protein/ adjuvant was administered to 1 Balb C mouse and 1 Swiss Webster mouse, and adjuvant alone was administered to 1 Balb C mouse and 1 Swiss Webster mouse. Sera included in the data of Table IV represent the specimens collected 16 weeks after the final innoculation of each mouse.

All sera were stored at −70° C. in small aliquots, to minimize the effects of repeated freeze-thaw.

ELISA

The ELISA protocol has been rigidly standardized and statistically evaluated (see, e.g., Rodman et al., 1993, Proc. Natl. Acad. Sci. USA, 90:7719; Rodman et al., 1997, supra). Each serum/antigen was tested in a minimum of 3 separate assays. The corrected serum O.D. for each antigen represented the read-out O.D. of the serum/antigen minus the O.D. of serum background (0 antigen). Corrected O.D. of 0.10 was considered positive. If corrected O.D. was 0.08–0.15, the assay was repeated 3 additional times. For assays of human and chimpanzee sera, a single standard serum (ST) was included on each titer plate and the final titer was calculated as X/ST. In these assays peroxidase labeled anti-human IgG or IgM (KPL) were used as secondary antibodies. Peroxidase labeled anti-monkey IgM or IgG (KPL) secondary antibodies were found to be non-reactive with chimpanzee sera, but were used for all other simian sera tested. The anti-mouse IgM or IgG (Sigma) and anti-rabbit IgM or IgG (KPL) were used to assay mouse and rabbit sera, respectively. Since the peroxidase labeled antibodies for each species were raised in goat, the ELISA included an extra blocking step, i.e., 1% normal goat serum was applied following the antigen wash and prior to application of the species-specific test serum, to ensure that no part of the displayed reactivity was attributable to goat antibodies.

TABLE IV

Titer and Epitope Analysis of anti-Tat Antibodies

| | | IgM Peptide: | | | | IgG Peptide: | | | |
|---|---|---|---|---|---|---|---|---|---|
| Species | # of Sera | 1 | 4 | 8 | Tat | 1 | 4 | 8 | Tat |
| Humans | | | | | | | | | |
| Males | 40 | 0 | 40 | 38 | 40 | 0 | 38 | 31 | 38 |
| Females | 40 | 0 | 40 | 40 | 40 | 1 | 40 | 36 | 40 |
| HIV + | 60 | 0 | 60 | 46 | 60 | 1 | 60 | 21 | 60 |
| Chimps | | | | | | | | | |
| Males | 11 | 0 | 11 | 10 | 11 | 0 | 11 | 9 | 11 |
| Females | 11 | 0 | 11 | 11 | 11 | 0 | 11 | 8 | 11 |
| HIV + | 2 | 0 | 2 | 2 | 2 | 0 | 2 | 2 | 2 |
| Simians | | | | | | | | | |
| Monkeys | 32 | 0 | 0 | 0 | 0 | 0 | 32 | 2 | 21 |
| SIV + | 3 | 0 | 0 | 0 | 1 | 0 | 3 | 3 | 3 |
| Rabbits | | | | | | | | | |
| Normal | 30 | 0 | 2 | 0 | 0 | 0 | 3 | 0 | 0 |
| Tat + | 1 | 1 | 0 | 0 | 1 | 1 | 1 | 0 | 1 |
| Mice | | | | | | | | | |
| Normal | 30 | 0 | 0 | 0 | 0 | 0 | 2 | 0 | 1 |
| Adj. Only | 2 | 0 | 0 | 0 | 0 | 0 | 0 | 0 | 0 |
| Tat + | 2 | 0 | 0 | 0 | 0 | 2 | 0 | 0 | 2 |

Results

Human

Figure 6A:
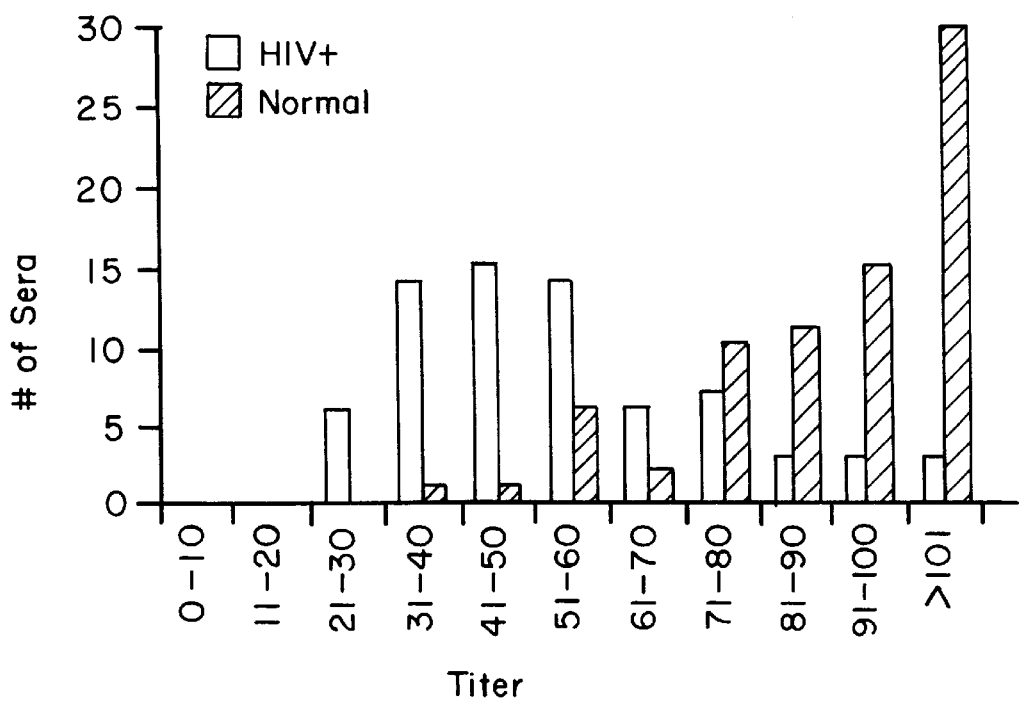
FIGS. 6A and B. ELISA analysis of IgM (A) and IgG (B) reactivity of two cohorts of 70 different human sera, HIV+ and HIV− (normal), with Tat protein of HIV-1. The HIV+ cohort was assembled from sera collected prior to 1994, therefore the characteristics are not attributable to the anti-HIV medications in use since that time. Each assay plate included both HIV+ and HIV− specimens and a single normal serum (ST). The recorded titer for each serum (X) represents X/ST. The titers are grouped in intervals of 10 with the number of sera of each cohort designated for each interval. The distributions of both IgM and IgG titers for the HIV+ sera are skewed to the lower intervals, particularly those of the IgM.
Figure 6B:
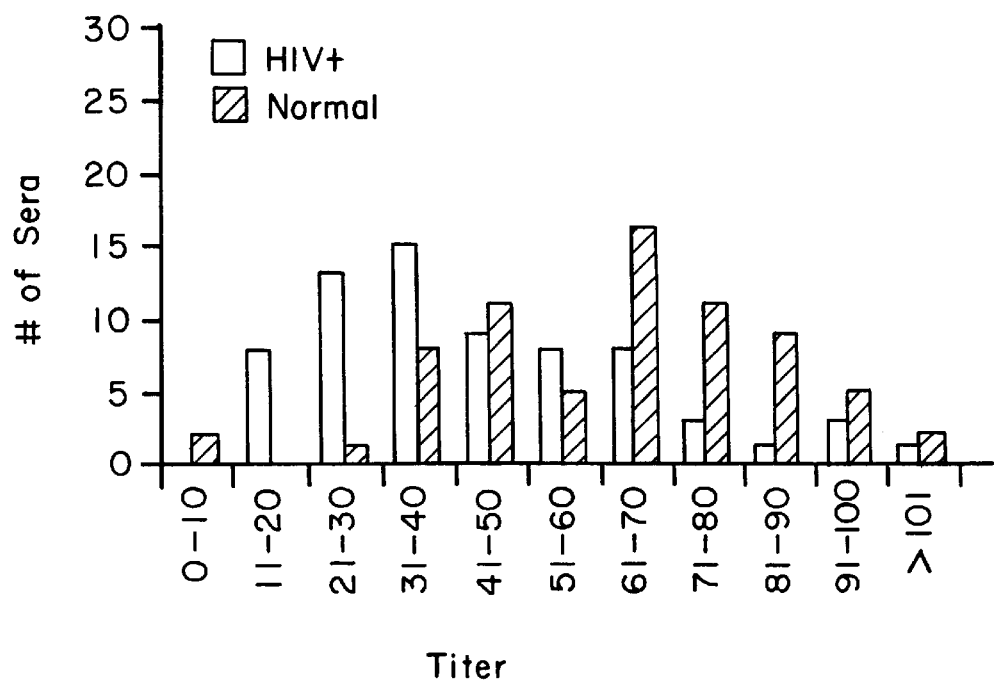

FIG. 6 presents the ELISA assay data of IgM and IgG reactivity with Tat protein of HIV+ and HIV− (normal) sera. As noted in Materials and Methods section, those HIV+ sera were collected from individuals who had not received any anti-HIV medication other than that in general use prior to mid- 1994 (e.g., AZT). Comparison of the titers of the two cohorts of 70 sera each, shows that the IgM titers (FIG. 6A) of the HIV+ cohort are at significantly lower levels than those of the HIV− cohort. The distribution of the Tat-reactive IgG titers of the same sera, however, appears to be random both with respect to comparison of the two cohorts (FIG. 6B) and in individual sera (not shown). Some of those IgG titers were sufficiently high and may reflect the presence of the maturation forms of the natural antibodies (Coutinho et al., 1995, Curr. Opinion Immunol., 7:812; Parker et al., 1996, Human. Immunol., 45:94) or antibodies independently induced by unrelated antigens with sequences similar to the antigenic epitopes of Tat protein.

The epitope analysis of sera of each of the two human cohorts (Table IV) shows that the entire IgM reactivity with Tat protein is limited to two non-adjacent sequences: one including peptides 4 and 5 which span the cysteine(Cys)-rich region, and the other including peptides 7, 8 and 9 which span the arginine (Arg)-rich region (FIG. 5). In accord with the data of Table IV, all tested HIV− (normal) males and females have significant titers of IgM reactive with Tat protein as well as with the epitope represented by peptide 4, and all but 2 have significant titers with the epitope represented by peptide 8. Similarly, all of the tested HIV+ sera have low, but significant, titers of IgM antibodies reactive with Tat protein and the epitope represented by peptide 4. In contrast, of the 60 samples of HIV+ sera, only 46 show some very low levels of IgM reactivity with the Arg-rich sequence represented by peptide 8. In all experiments, the IgG titers (Table IV) do not completely correlate with IgM titers, probably reflecting the reactivity with peptide 1 (see sequence in FIG. 5) present in one HIV− serum and one HIV+ serum, and therefore not Tat-induced.

Figure 7A:
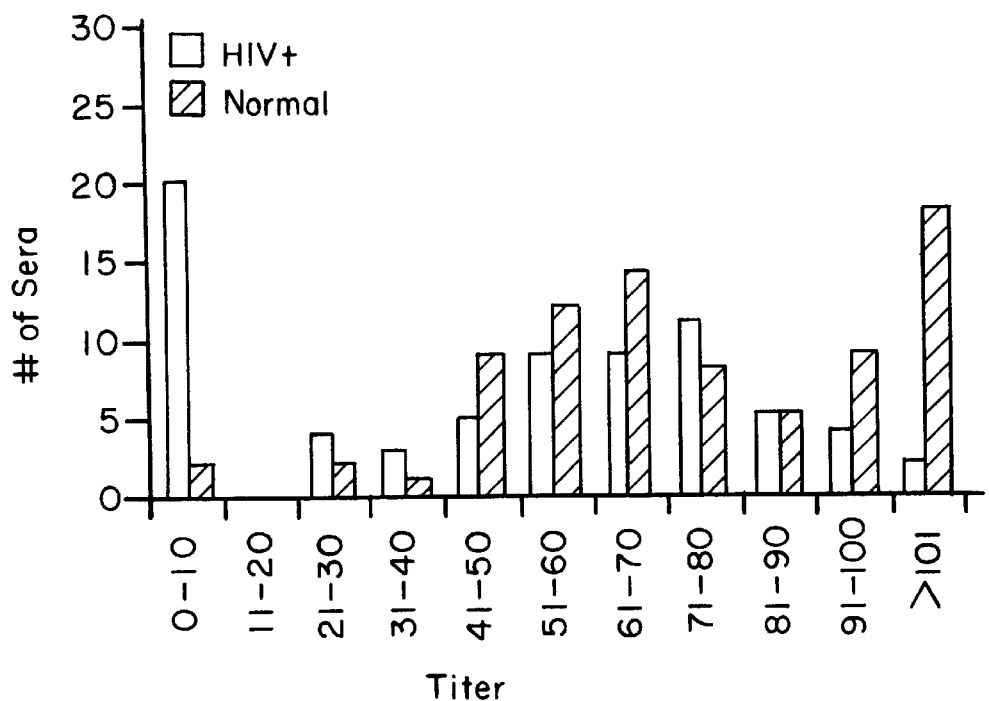
FIGS. 7A and B. The distribution of titers of IgM (A) and IgG (B), reactive with arginine-rich Tat-derived peptide 8 (from FIG. 5) in two cohorts of 70 human sera, HIV+ and HIV− (normal), correlates with the pathoprogression of HIV-1 infection.
Figure 7B:
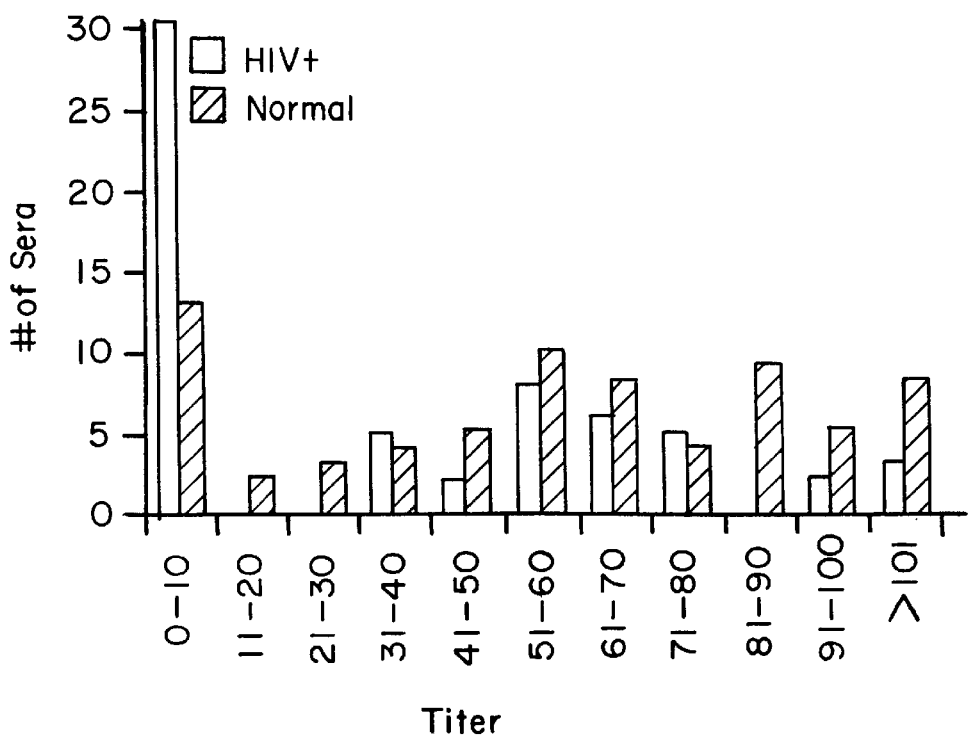
Figure 8A:
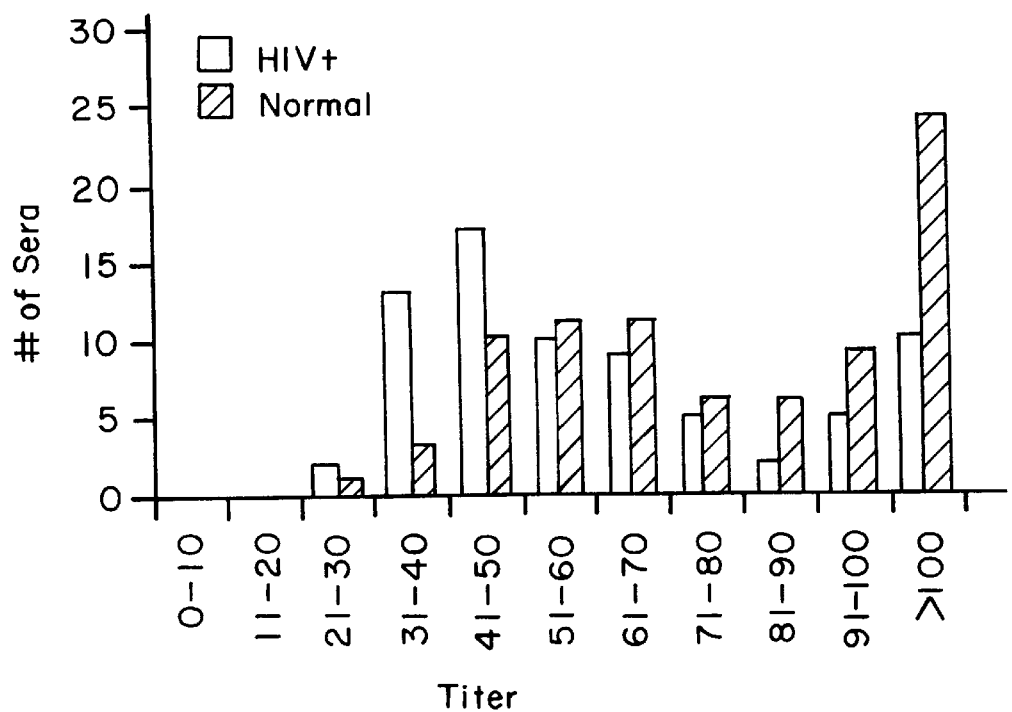
FIGS. 8A and B. The distribution of titers of IgM (A) and IgG (B) reactivity with cysteine-rich Tat-derived peptide 4 (from FIG. 5) in two cohorts of 70 human sera, HIV+ and HIV− (normal), correlates with the pathoprogression of HIV-1 infection but less stringently than that demonstrated for peptide 8 (FIG. 7).
Figure 8B:
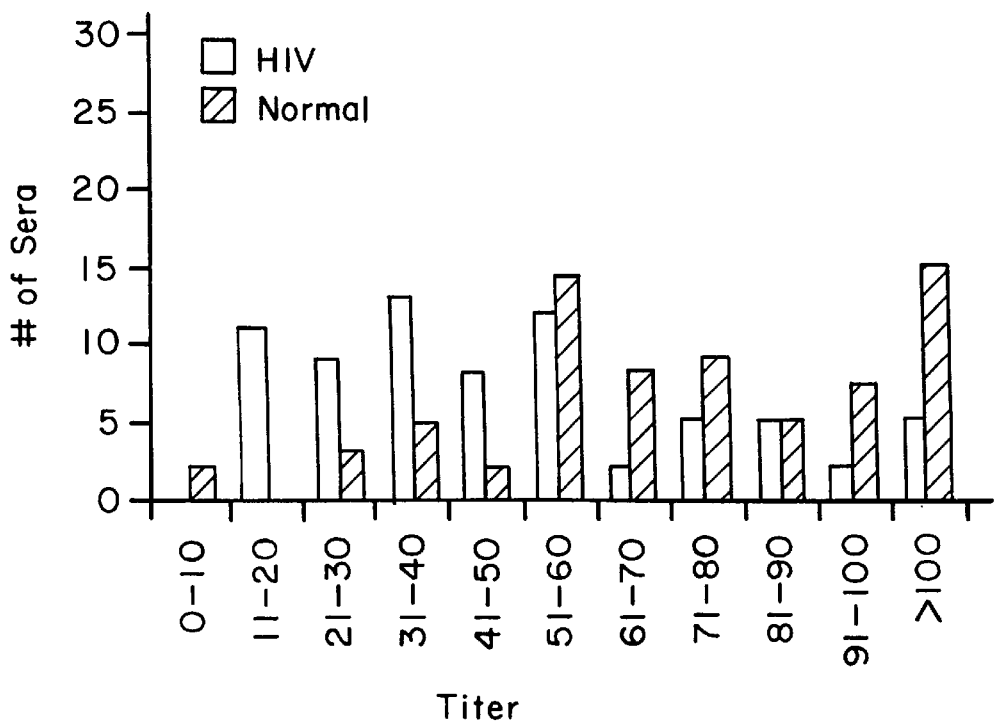

The data of FIGS. 7 and 8 confirm that the decline of the Tat-reactive natural antibodies in HIV+ sera is more stringently reflected in relation to peptide 8 (FIG. 7) than in relation to peptide 4 (FIG. 8).

Figure 9A:
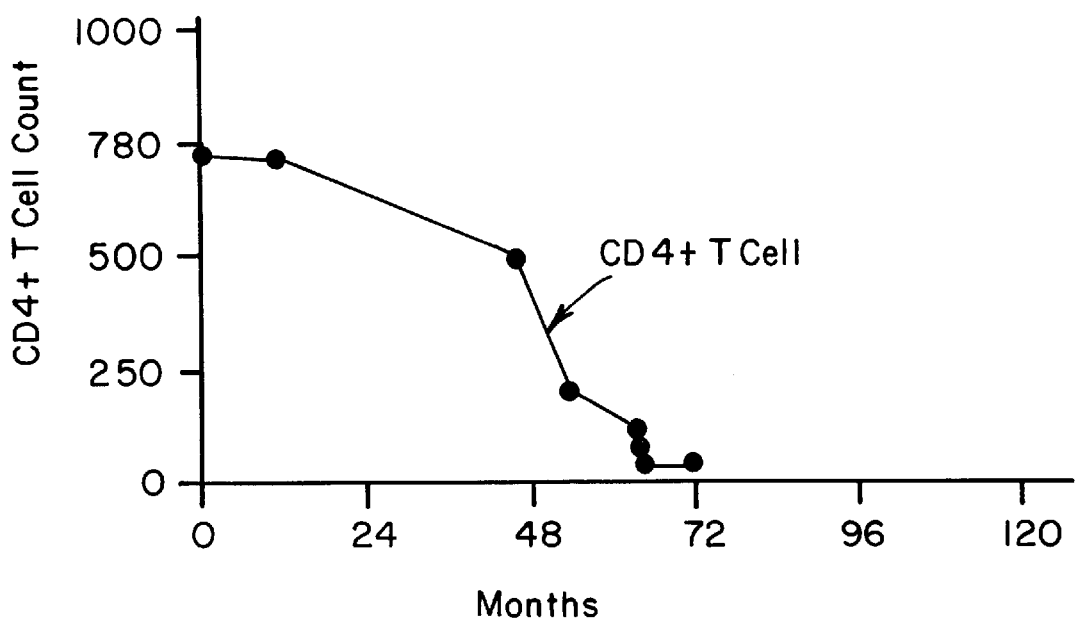
FIGS. 9A and B. Analysis of CD4+ T cell counts (A) and of the titers of IgM reactivity (B) with HIV Tat protein, and with Tat-derived peptides 4 and 8 (from FIG. 5) in serial specimens from an HIV+ male over a period of five years preceding his death with the diagnosis of AIDS. Each specimen for CD4+ T cell count was obtained at the same time as that for the serum analysis.
Figure 9B:
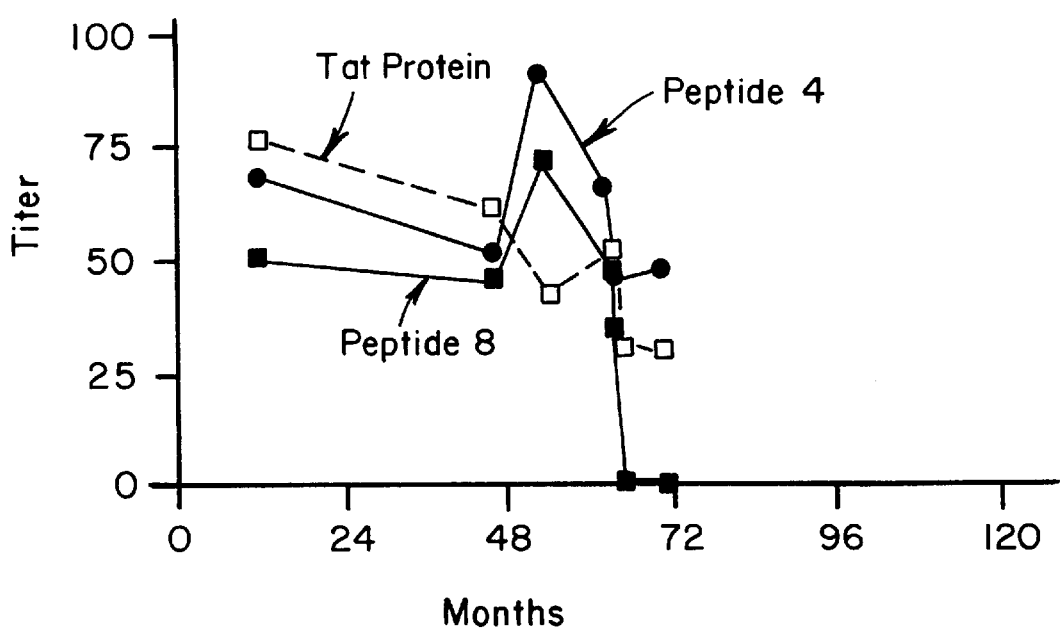
Figure 10A:
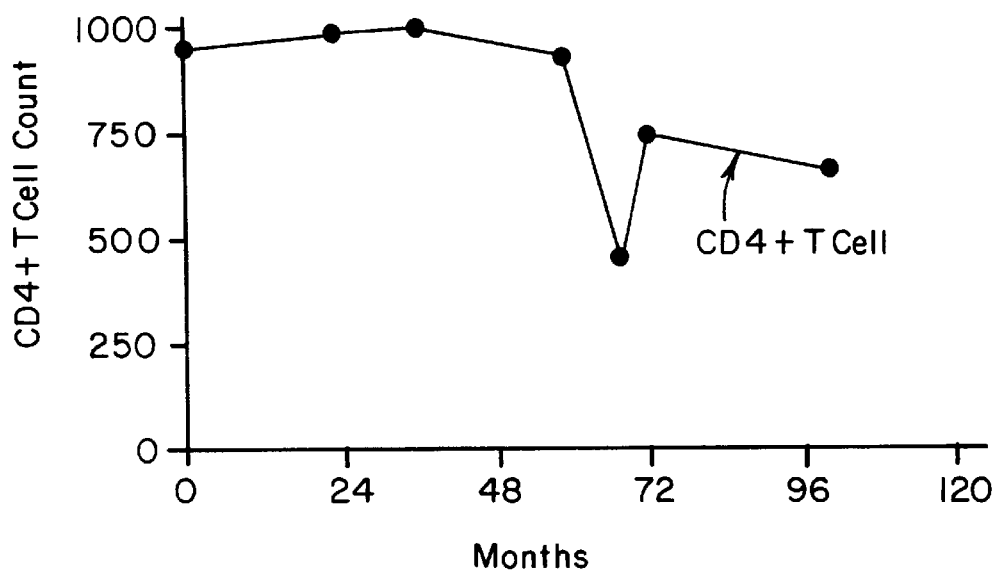
FIGS. 10A and B. Analysis of CD4+ T cell counts (A) and of the titers of IgM reactivity (B) with HIV-1 Tat protein, and with Tat-derived peptides 4 and 8 (from FIG. 5) in serial specimens of sera, collected over a period of 9 years, from an HIV+ male whose duration of infection is estimated to be over 11 years, but who has displayed no HIV-associated pathology and who has had no anti-HIV medication. Each specimen for serum analysis was obtained at the same time as that for CD4+ T cell count.
Figure 10B:
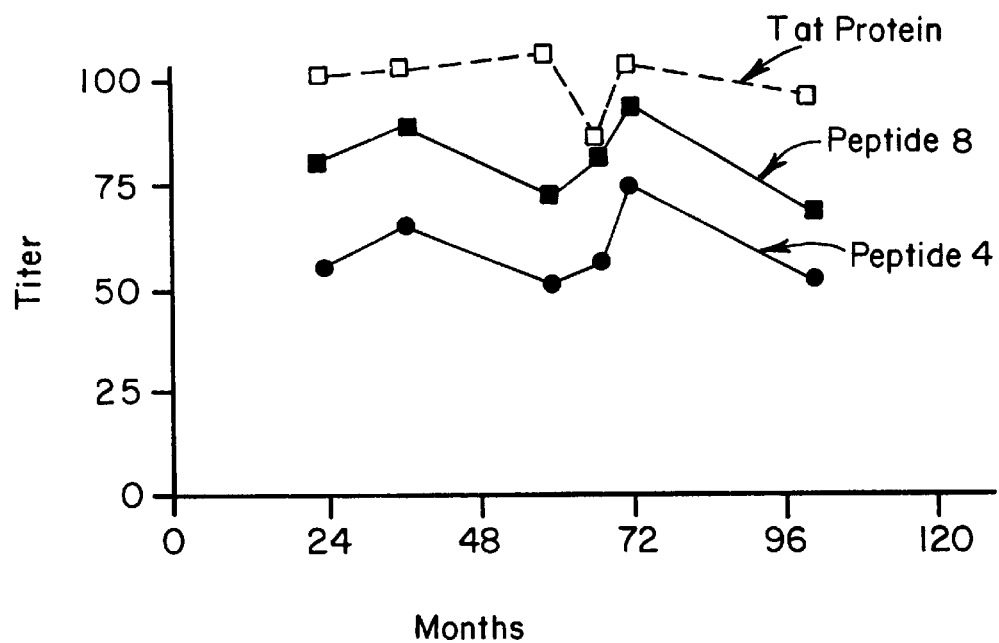
Figure 11A:
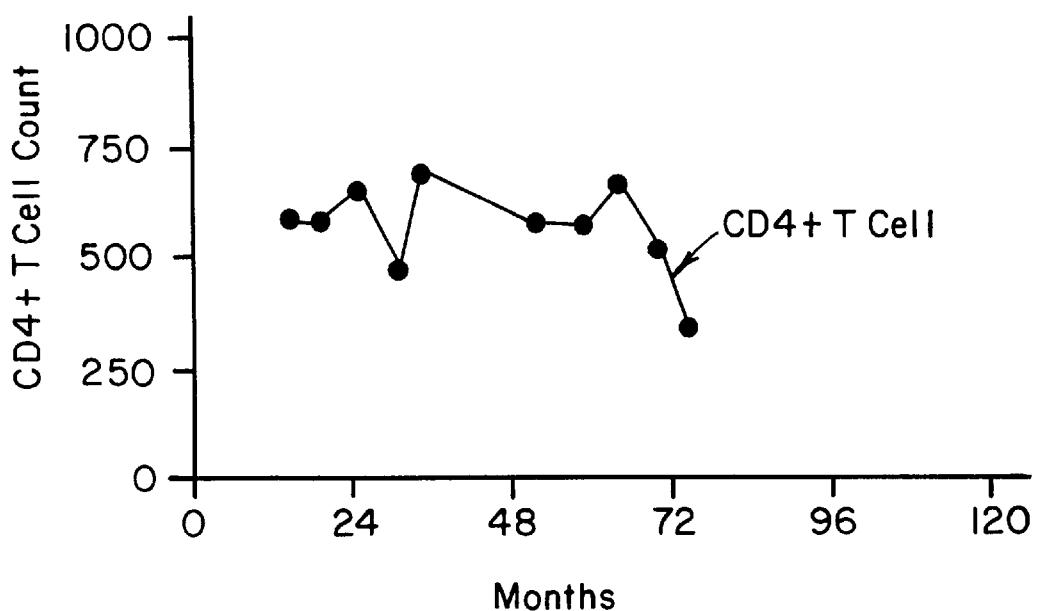
FIGS. 11A and B. Analysis of CD4+ T cell counts (A) and of the titers of IgM reactivity (B) with HIV-1 Tat protein, and with Tat-derived peptides 4 and 8 (from FIG. 5) in serial specimens of sera from an HIV+ male. Following the analysis of specimen 4, in which decline of CD4+ T cell count was noted, anti-HIV therapy was initiated. The CD4+ T cell count in specimen 5 was taken after 6 months of therapy.
Figure 11B:
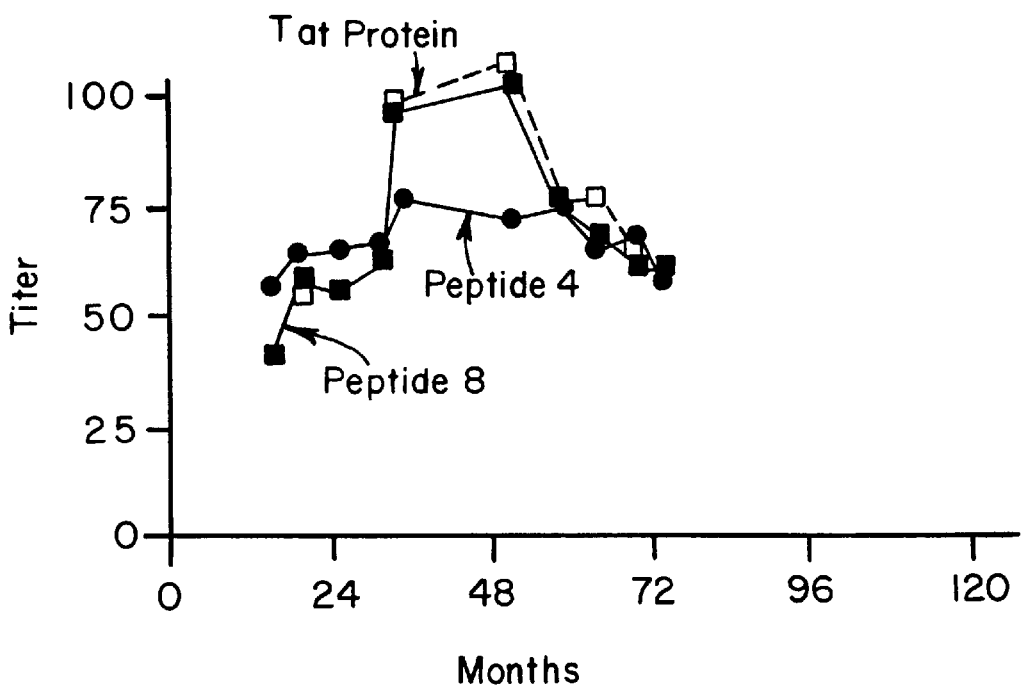

The correlation of the titers of Tat-reactive IgM natural antibodies with the pathoprogression of HIV infection and with the CD4+ T cell count, an established index of that progression (Samuelsson et al. ,1997, Virology 238:180), is shown in FIGS. 9, 10 and 11. Each Figure is a display of data obtained from serial specimens of a single individual, including IgM titer assays for Tat protein, peptide 4, peptide 8 and clinical laboratory report of CD4+ T cell counts.

The series in FIG. 9 is that from an HIV+ male collected over a period of five years preceding his death with a diagnosis of AIDS. Each value for Tat protein IgM titer reflects the combination of the peptide 4 and peptide 8 IgM values for the same specimen. Particularly striking is the sharp rise followed by the precipitous drop in the peptide 8 reactivity concurrent with the virtual elimination of the CD4+ T cells in the specimen collected 8 months prior to death.

FIG. 10 is a display of data of the series of specimens from an HIV+ male whose duration of infection is estimated at over 11 years and who has had no anti-HIV medication and no symptoms of HIV pathogenesis and, thus, fits the criteria of long-term-survivor (LTS) or long-term-non-progressor (LTNP) (Cao et al., 1995, New Eng. J. Med., 332:201; Montefiori et al., 1996, J. Infect. Dis., 173:60). In this patient, the pattern of maintenance of titers of the IgM natural antibodies reactive with Tat protein, peptide 4 and peptide 8 are similar to those defined for normal (HIV−) humans (Rodman et al., 1992 and 1997, supra). The high anti-Tat titers, particularly those for peptide 8, are correlative with the maintenance of CD4+ T cell counts within the normal range.

Similar correlation is shown in the series of specimens (FIG. 11) from a single HIV+ individual for whom antiviral therapy was initiated following report of decline in CD4+ T cell count. Following a period of medication, both CD4+ T cell count and the titers of the natural antibodies, particularly those reactive with peptide 8, rose. The successive specimens from that patient showed maintenance of both CD4+ T cell counts and antibody titers in the normal range, in correlation with a generally good clinical status.

Chimpanzee

The sera of all of the 22 normal chimps had significant titers of both IgM and IgG antibodies reactive with Tat protein and peptide 4 (Table IV). When assayed with peptide 8, 21 of that group displayed significant IgM and 17 displayed significant IgG reactivity. The sera of each of the two HIV-inoculated chimps displayed significant IgM and IgG reactivity with Tat protein and with peptide 4, but a much lower IgM reactivity with peptide 8. It can be concluded therefore that the natural antibody repertoire of chimpanzee is similar to that of humans.

Monkey

No IgM reactive with Tat protein or any of its constituent peptides was detected in any of the 32 normal simian sera (Table IV). Of the 3 SIV-infected monkeys, only one showed IgM reactivity with Tat protein and none showed IgM reactivity with any of the peptides. All 32 sera, however, displayed IgG reactivity with peptide 4, and 21 of those displayed IgG reactivity with the Tat protein. Two sera of the normal macaques and all three of the SIV-infected macaques displayed IgG reactivity with peptide 8.

Rabbit

Of the 30 normal rabbit sera, only two samples displayed IgM reactivity with peptide 4 (Table IV). This reactivity, however, was not accompanied by a detectable IgM reactivity with Tat protein. Those two peptide 4-reactive sera and an additional normal rabbit serum displayed IgG reactivity with peptide 4 but, again, not with Tat protein. A single tested Tat-immunized rabbit serum displayed both IgM and IgG reactivity with peptide 1 and with Tat protein as well as the IgG reactivity with peptide 4.

The absence of correlation between peptide 4 and Tat protein reactivity in both normal and Tat-immunized rabbit sera suggests that the peptide 4 IgM and IgG reactivity reflects a response to an exogenous Tat-unrelated antigen. In contrast, the IgM and IgG reactivity of the serum of the Tat-immunized rabbit with peptide 1 correlates with the reactivity with Tat protein and is therefore attributable to induction by the immunogen.

Mouse

Of the sera from 30 normal mice, two Tat/adjuvant-immunized mice and two adjuvant-only-immunized mice, none displayed IgM reactivity with Tat protein or any of the peptides (Table IV). Two of the 30 normal mouse sera displayed IgG reactivity with peptide 4, and the serum of another mouse displayed IgG reactivity with Tat protein. The sera of the two mice immunized with adjuvant/only displayed no reactivity while the sera of the two mice immunized with Tat/adjuvant displayed exceedingly high (>1.0) activity with peptide 1 and with Tat protein. It can be concluded that, analogously to rabbit, Tat protein is a potent inducer of an antibody response in mouse specifically directed to the sequence displayed in peptide 1.

Discussion

It has been demonstrated by various researchers that HIV-1 Tat protein plays an important role early in the pathogenetic sequence of HIV infection. Thus, evidence from various in vitro studies indicates that Tat participates in viral internalization, mediated primarily by the basic domain represented by Tat peptides 7, 8, and 9 (FIG. 5; Frankel and Pabo, 1988, Cell, 55:1189; Vives et al., 1997, J. Biol. Chem., 272:16010). Intracellular propagation of the virus is also dependent upon Tat through its interaction with the Tar region of the viral RNA, resulting in transactivation (Kuppuswamy et al., 1989, Nucl. Acids Res., 17:3551; Cullen, 1991, Ann. Rev. Microbiol., 45:219). The Cys-rich region of Tat, represented by Tat peptides 4 and 5 (FIG. 5) plays an essential role in Tat/Tar binding and the consequent replication of HIV genome (Kuppuswamy et al., supra; Cullen, supra). Another pathogenic activity of Tat, well documented in vitro, is that of induction of apoptosis (see Example 5 and Samuelsson et al., supra).

It can be concluded, based on the present invention, that the pathogenic activities of Tat are dependent upon the Tat sequences that include the epitopes for the two natural IgM antibodies which are present in all human and chimpanzee sera, but are not present in the sera of other mammals, e.g., monkeys, rabbits, and mice (Table IV).

It can be therefore proposed that those natural IgM antibodies provide, or contribute to, a mechanism of resistance to HIV pathogenesis in the early post-HIV infection period in the human host. Retardation of viral entry, replication and virus-induced apoptosis by those antibodies in the human host and the absence of that retardation in rhesus macaques may account for the observations that T lymphocyte turnover in SIV-infected rhesus macaques occurs at a considerably higher rate than that in HIV-infected humans (Mohri et al., 1998, Science, 279:1223; Rosenzweig et al.,1998, Proc. Natl. Acad. Sci. USA, 95:6388). The proposition that the Tat-reactive natural antibodies may impede the action of Tat, and thereby contribute to maintenance of the early period of apparent latency following HIV infection, is supported by the observation that persons designated LTS (long-term survivor) (Cao et al., supra) or LTNP (long-term non-progressor) (Montefiori et al., supra) show little evidence of T cell apoptosis (Matzinger, supra) and, as disclosed in the present invention (FIG. 10), maintain normal levels of the natural antibodies.

Although the precise mechanisms whereby the CD4+ T cell population is depleted in the peripheral blood of HIV+ humans are not yet specifically established, a relationship between the CD4+ T cell count and titers of the Tat-reactive natural antibodies is demonstrated in the serial specimens of FIGS. 9, 10, and 11 of this study. In each series, the CD4+ T cell counts parallel the maintenance or drop of the antibody titers.

It should be noted, however, that, as evident from the pathoprogression of AIDS, the arrest of Tat-related pathogenicity by anti-Tat natural antibodies may be limited due to the immune system recognition of the Tat-derived epitopes as "self" antigens leading to the induction of tolerance (Matzinger, 1994, Ann. Rev. Immunol., 12:991; Van Parijis and Abbas, 1998, Science, 280:243). Although poorly understood, the fundamental and implemental event of self-tolerance appears to be that of deletion, or turning off, of the T and/or B cells involved in natural antibody production (Klein et al., 1998, J. Exp. Med., 188:5). Thus, as the Tat antigen load is increased, the production of Tat-reactive natural antibodies may be stifled, antibody-mediated restriction of the aggressive activities of Tat lost, and the period of pathoprogressive latency terminated.

The IgM- and IgG-reactive epitope similarity for the anti-Tat human natural antibodies disclosed in the present invention suggests that each represents a pair of isotypes of the same antibody. The disclosed constancy of the IgM titers, but not of the IgG titers, of these antibodies in serial specimens from normal individuals (Table IV), indicates that the IgM is the homeostasis-maintaining isotype (see also Rodman et al., 1997, supra).

Although, at present, the mechanism and utility of class switch of natural antibodies are not well understood (Medzhitov and Janeway, 1997, Cur. Opinion Immunol., 9:4) making the assignment of separate roles to the IgM and IgG isotypes of the human Tat-reactive natural antibodies difficult, it is disclosed in the present invention that, in HIV+ humans, Tat-reactive antibodies attributable to immunogenic induction do not occur (Table IV). Since Tat-reactive antibodies are induced in virus-infected monkeys and in Tat-immunized rabbits and mice (Table IV), it appears that the failure to induce anti-Tat antibodies is unique to the human immune system. The attribution of that uniqueness to genetic specificity is supported by a similar profile of Tat-reactive antibodies in the sera of pre- and post- HIV-infected chimps (Table IV) who are presumed to have high level of genetic identity with humans (Crouau-Roy et al., 1996, Hum. Mol. Genet., 5:1131).

Example 5

Analysis of the Ability of Natural Anti-Tat Antibodies and their Monoclonal Counterparts to Inhibit Tat-induced T Cell Apoptosis Materials and Methods Peptides Tat-derived peptides (see sequences in FIGS. 5 and 12) were prepared as described previously (Rodman et al., 1993 and 1999, supra).

Apoptosis Assays

Tat-induced T cell apoptosis was tested in PBL of blood specimens obtained from normal human volunteers, collected by standard Ficoll Hypaque procedure and plated in 0.5-ml aliquots, at a density of $10^6$ cells/ml. After 2 hour incubation at 37° C., the appropriate additions to each well, as noted (FIGS. 13, 14) were made. After 3 days of incubation, the contents of each well were harvested, washed, fixed in cold EtOH, washed, stained with propidium iodide/RNAase and the fluorescence was measured by flow cytometry as previously described (Park et al., 1996, Exp. Cell Res., 226:1; Darzynkiewicz et al., 1992, Cytometry, 13:619). The apoptotic cells were identified as T cells by typical gating of forward and sideward scatter and by additional CD3 staining (Lecoeur et al., 1998, J. Immunol. Meth., 217:11).

To assay the effect of species-specific IgM pools on Tat-induced apoptosis of human T cells, each IgM pool was obtained from circulating blood of individual human adult females (HF) and males (HM), a pool of human cord bloods (HCB), individual chimpanzee females (CF) and males (CM), individual rhesus females (RF) and males (RM). The mouse IgM pools were derived from combined blood specimens of male, female and juvenile Swiss Webster mice (SWM) and of Balb C mice (BCM). The species-specific IgM pools were collected by standard techniques (e.g., as described by Messmer et al.,1999, J. Immunol., 162:2184), with the modification that Sephacryl 300 (Pharmacia) was used as the size-exclusion gel.

To measure the inhibition of Tat- and Tat peptide-induced apoptosis by human cord blood B cell-derived monoclonal antibodies (Mabs), 1 µg of the designated Mab (produced by hybridomas described in Example 3) and 0.6 µM of the designated peptide or Tat protein was added to each well containing PBL.

The tested cells represented groupings of PBL from three or four normal adult humans, so that each set of assays using different IgM pools or Mabs was carried out on the same set of substrate cells. The Tat inhibition capacity of each IgM pool or Mab was assayed a minimum of 3 times, the average calculated and the SRM determined.

ELISA

ELISA assays were performed as described in Example 4. Each IgM pool was assayed for reactivity with Tat protein or Tat-derived peptides 3 times, and the interaction was considered positive ("+", Table V) if a mean value of the O.D. was >0.10.

TABLE V

Reactivity of the Specific IgM Pools with Tat-derived Peptides

| | Peptides | | | | | | | | | | | | Tat |
|---|---|---|---|---|---|---|---|---|---|---|---|---|---|
| | 1 | 2 | 3 | 4 | 5 | 6 | 7 | 8 | 9 | 10 | 11 | 12 | Protein |
| Human IgM Pool | | | | | | | | | | | | | |
| F1 | – | – | – | + | + | – | + | + | + | – | – | – | + |
| F2 | – | – | – | + | – | – | + | + | – | – | – | – | + |
| F3 | – | – | – | + | + | – | + | + | + | – | – | – | + |
| M1 | – | – | – | + | + | – | + | + | + | – | – | – | + |
| M2 | – | – | – | + | – | – | + | + | + | – | – | – | + |
| FCB | – | – | – | + | – | – | + | + | + | – | – | – | + |
| Chimp IgM Pool | | | | | | | | | | | | | |
| F1 | – | – | – | + | + | – | + | + | – | – | – | – | + |
| F2 | – | – | – | + | – | – | + | + | – | – | – | – | + |
| M1 | – | – | – | + | + | – | + | + | + | – | – | – | + |
| M2 | – | – | – | + | – | – | + | + | + | – | – | – | + |
| Rhesus IgM Pool | | | | | | | | | | | | | |
| F1 | – | – | – | – | – | – | – | – | – | – | – | – | – |
| F2 | – | – | – | – | – | – | – | – | – | – | – | – | – |
| M1 | – | – | – | – | – | – | – | – | – | – | – | – | – |
| M2 | – | – | – | – | – | – | – | – | – | – | – | – | – |
| Mouse IgM Pool | | | | | | | | | | | | | |
| Balb C | – | – | – | – | – | – | +/– | – | – | – | – | – | – |
| Swiss | – | – | – | – | – | – | – | – | – | – | – | – | – |

Results

As shown in Examples 3 and 4 and in earlier studies (Rodman et al., 1993 and 1999, supra), the epitope recognition of Tat-reactive antibodies by normal (HIV–) human sera is encoded in peptides 4 and 5, representing the Cys-rich sequence and peptides 7, 8 and 9, representing the Arg-rich sequence. Consistently with these observations, we have demonstrated in the present invention (FIGS. 12A, B) that the apoptosis-inducing capacity of Tat protein is mainly mediated by the Arg-rich sequences with an Arg density of at least 3/12: peptide 7, Arg=3, peptide 8, Arg =6, Peptide 9, Arg =5, with the greatest apoptosis induction by peptide 8. Significant, but comparatively low apoptosis inducing capacity was also demonstrated by Cys-rich peptide 4 and, clearly, none was attributable to peptide 1 or peptide 11 (FIG. 12) nor to any of the other Tat-derived peptide disclosed in the instant invention. (data not shown). Measurements of apoptotic response to equivalent molar doses of Tat protein and peptide 8 (FIG. 12C) show that the percentage of cells in a specific population capable of being induced to apoptosis is fixed, and the full capability is expressed in response to a defined molar dose of Tat protein or its equivalence of peptide 8.

The data in FIG. 13 demonstrate the capacity of Tat protein to induce apoptosis of human T cells and the ability of all human and chimp IgM pools to suppress this Tat-induced apoptosis within the range of 70–80%. This inhibitory effect of human and chimp IgM is highly species-specific as no IgM pool of rhesus or mouse showed any inhibition of Tat-induced apoptosis of human cells (FIG. 13). In fact, in the presence of rhesus and mouse IgM, the apparent increase in apoptosis was observed (shown as a negative value of the anti-apoptotic effect) which may be attributed to the introduction of some species-specific apoptosis-inducing component.

ELISA measurements of the reactivity of the IgM pools with each of the Tat-derived peptides (see sequences in FIGS. 5, 12) showed concordance of epitope recognition and the ability to inhibit Tat-induced apoptosis (Table V, FIG. 13). All human and chimpanzee IgM pools displayed the presence of IgM reactive with the Cys-rich sequence (peptides 4 and 5), the Arg-rich sequence (peptides 7, 8, and 9) and with Tat protein (Table V), consistent with the display of inhibition of apoptosis by those pools (FIG. 13). The rhesus IgM pools, which displayed no inhibition of the Tat-induced apoptosis (FIG. 13) showed no reactivity with Tat protein or its component peptides (Table V). However, as a corrected ELISA value of >0.10 has been designated significant, the display of reactivity 0.10 (a mean of 3 assays) by one of the mouse IgM pools (Balb C, Table V) indicated the need to examine the 30 individual murine sera from which that IgM pool was assembled. Of those, only the sera of two of the adult breeder females were reactive with Tat peptide 8. By further testing (data not shown) those sera displayed even greater reactivity with a peptide representing an Arg-rich sequence of mouse protamine (the sperm-specific DNA binding protein) and is therefore likely to be induced by this or some other Tat-unrelated antigen.

In the next series of experiments (FIG. 14) we have measured the inhibition of Tat- and Tat peptide-induced apoptosis by human cord blood B cell-derived monoclonal antibodies (Mabs) disclosed in Example 3. The "no Mab" set confirmed that Tat protein and peptide 8 vigorously induce apoptosis, while the apoptotic induction by peptide 4 was relatively minor. Surprisingly, Tat protein-induced apoptosis was inhibited not only by Mab 8 (specifically reactive with Arg-rich peptide 8) but also by Mab 4 (specifically reactive with Cys-rich peptide 4). To demonstrate the specificity of the Mab 8- and Mab4-mediated inhibition, a non-Tat-reactive Mab LF (disclosed in Examples 1 and 2) was tested and showed no capacity to inhibit Tat-induced apoptosis.

Figure 14B:
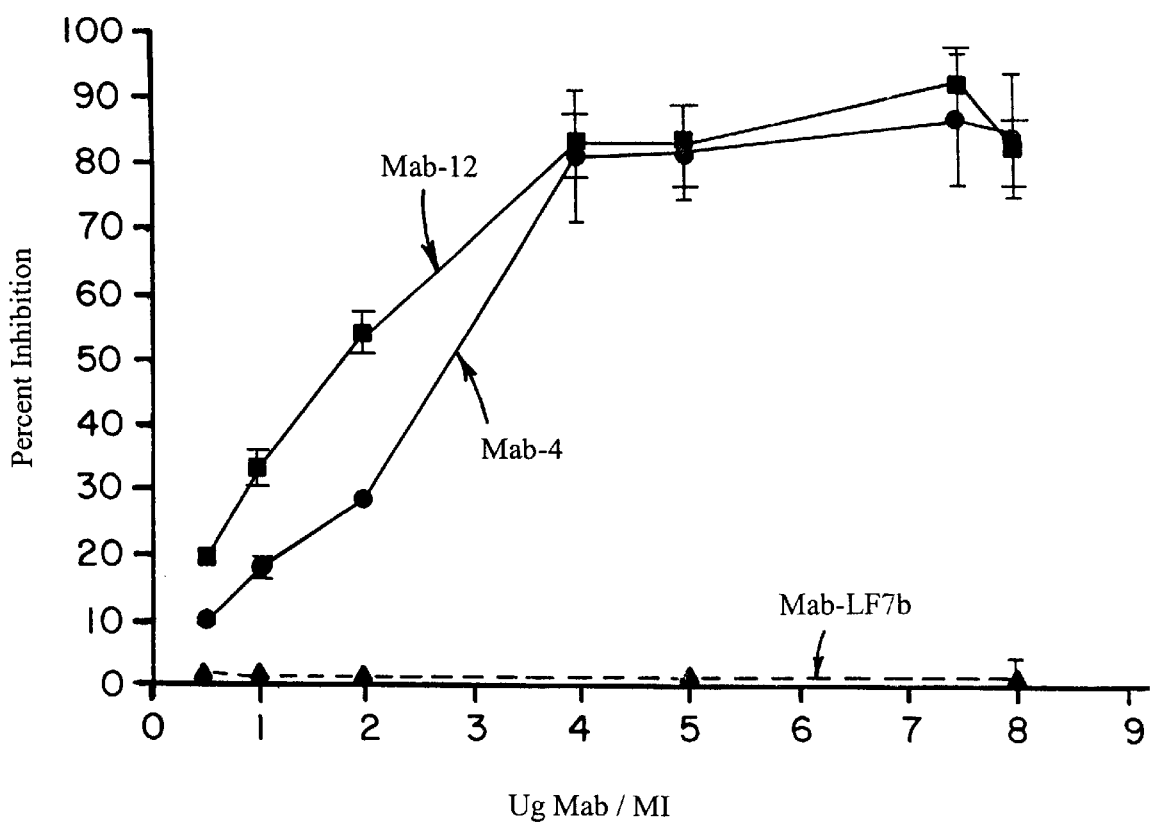
FIGS. 14A and B. Inhibition of Tat and Tat peptide-induced apoptosis by human cord blood B cell-derived monoclonal antibodies (Mabs). Each bar represents a well containing human PBL to which the designated peptide or Tat protein and the designated Mab were added. Mab4—Mab specifically reactive with Tat-derived peptide 4; Mab8—Mab specifically reactive with Tat-derived peptide 8; MabLF—a non Tat-reactive Mab previously shown to be reactive with a fraction of lactoferrin (LF). A. Determination of percentage of apoptotic cells in the samples. B. Determination of percent inhibition in the samples.

Further confirmation of the specificity was provided by the analysis of the inhibition of Tat-induced apoptosis in response to Mab identity and dose. Although the apoptotic effect of peptide 4 was considerably less than that of peptide 8, the ability of both Mabs to inhibit Tat protein-induced apoptosis was similar. A reasonable explanation for such seeming anomaly is that the binding of Mab 4 to the peptide 4 region of the Tat protein may provide a hindrance to the Tat protein/T cell interaction and, in this way, prevent the initiation of an apoptotic sequence. This possibility is supported by the demonstration of a greater inhibition of peptide 8-induced apoptosis by Mab 8 than by Mab 4 (FIG. 14). Peptide 8 provides no recognition site for Mab 4 and, thus, no basis for hindrance by Mab 4 of peptide 8/T cell interactions resulting in apoptosis. Although VDJ sequencing identified the heavy chain of Mab 4 as VH5 and that of Mab 8 as VH3, the greater degree of inhibition of Tat-induced apoptosis by Mab 8 cannot be attributable to its VH3 identity. Thus, as shown in FIG. 14, the Mab LF, which is also a member of the VH3 family (Rodman et al., 1997, Proc. Soc. Exp. Biol. Med., 216:404) did not exhibit any significant anti-apoptotic activity (FIG. 14).

Discussion

The apoptosis of B and T cells, commonly observed during HIV-1 infection, has been attributed to action by HIV protein Tat (Samuelsson et al., supra; Li etal., 1995, Science, 268:429). This activity of Tat is supported by the accumulating reports of its ability to induce programmed cell death in other tissues (e.g., the involvement of Tat in the neurodegeneration leading to dementia [Chen etal., 1997, J. Biol. Chem., 272:22385], the demonstration of Tat-induced apoptosis of human fetal neurons in culture [New et al., 1997, J. Neurovirol., 168], the observation of neuronal apoptosis in brain tissue from patients who had died with a diagnosis of AIDS [Wessenlingh et al., 1997, J. Neuroimmunol., 74: 1]).

It is disclosed in the present invention that in vitro an apoptosis-inducing activity of Tat is suppressed by isolated IgM fractions of normal human blood (FIG. 13) and, in a comparable mode, by the cord blood cell-derived monoclonal antibodies (Mabs; FIG. 14). This observation further establishes the correspondence of disclosed Mabs (Example 3) to the natural circulating Tat-reactive IgM and strongly suggests their clinical relevance as innate factors capable of combating HIV-1 infection.

As shown in Example 4, natural Tat-reactive antibodies are detectable in human and chimpanzee sera, but not in sera of other primates or mammals frequently used as animal models for studies of HIV pathogenesis and for development of vaccine or treatment modalities. The species-specificity of these natural anti-Tat antibodies is further supported by the present disclosure of the anti-Tat activities exhibited by the isolated IgM fractions of human and chimpanzee blood and the hybridoma-derived anti-Tat Mabs. Said activities are not manifested by IgM fractions isolated from the blood of rhesus macaques or of mice (FIGS. 13, 14). The demonstration of species-specificity of Tat-reactive Mabs as well as their effectiveness in suppressing Tat-induced destruction of human T cells further supports their potential clinical usefulness in treating and/or preventing the progression of AIDS.

Since there is now credible evidence that selective apoptosis is a normal metabolic mechanism of serving the need to control cellular accumulation and selective turnover (Lenardo et al., 1999, Ann. Rev. Immunol., 17:221; Tsubata, 1999, Int. Rev. Immunol., 18:347), it is logical to propose that specialized natural antibodies may play some role in the regulation of apoptosis. It can be further hypothesized that the system disclosed in the present invention—an apoptosis inducer of exogenous source (Tat) and an innate moderator (natural IgM antibodies) that, by happenstance, is capable of specific recognition of that inducer—may be a facsimile of a natural (human-specific) system of cell population control.

Example 6

A modification of the conventional method of hybridoma production for some cord blood cell hybridomas in addition to the conventional method was utilized. Thus, far, IgM secreting hybridomas have been prepared by that method, from 3 cord blood specimens and 2 HIV positive specimens. Other than determining that each secretes IgM, the antibody (presumaby monoclonal) has not been identified. I am not certain that there is any advantage other than one possibilityk, alluded to in the enclosed references 1, 2. We have determined that our Tat 9 ® rich epitope) Mab is $VH^3$. So, perhaps we can have a better yield of that Mab by the SAC method.

The modification is that of use of SAC, formalin treated *Staphyloccoccus aureus* (manufactured by SIGMA) as disclosed in Gore, M. M. et al, *Human Antibodies*, Vol. 8, 1 and Ikematsu, H. et al (Annals of the N.Y. Acad. Med. Vol. 764).

|    | CONVENTIONAL METHOD | | SAC MODIFICATION |
|---|---|---|---|
| 1. | Standard Ficol-hypaque procedure for isolation of PBL from non-clotted blood. | 1. | Same |
| 2. | Treat cells with cyclosporin A (c.A) + EBV (Epstein Barr Virus.) | 2. | Treat cells with c.A + SAC |
| Result: | T cells eliminated (cA effect) B cells stimulated and immortalized | Result: | T cells eliminated B cells stimulated but not immortalizee |
|    | Fusion with HMMA > monoclonal hybridoma | 3. | Same |

Treatment with SAC does not result in immortalization of the B cells that participate in the hybridoma, but SAC is a strong inducer of mitosis, so within a short period (72 hours vs 6 weeks) the cells are ready for fusion with the HMMA.

What is claimed is:

1. A method for producing human hybridoma cells which secrete monoclonal human natural IgM antibodies comprising the steps of:
   fusing immortalized or mitogen-stimulated umbilical cord blood cells with mouse: human heteromyeloma cells,
   isolating fused cells, and
   plating said fused cells under conditions of limited dilution, and recovering said hybridoma cells.

2. The method of claim 1 wherein said fused cells are hybridoma cells.

3. The method of claim 2 wherein said hybridoma cells produce monoclonal human natural IgM antibodies.

4. The method of claim 3 wherein said human natural antibodies are immunoreactive with human lactoferrin.

5. The method of claim 3 wherein said monoclonal human natural antibodies are immunoreactive with the Tat protein of HIV-1.

6. A human hybridoma cell which secretes human natural antibodies produced by the method of claim 1.

* * * * *